United States Patent
Fuller et al.

(12) 
(10) Patent No.: US 6,875,573 B2
(45) Date of Patent: Apr. 5, 2005

(54) DNA POLYMERASES HAVING AMINO ACID SUBSTITUTIONS AND HOMOLOGS THEREOF

(75) Inventors: Carl Fuller, Berkeley Heights, NJ (US); Joseph Szasz, Chardon, OH (US)

(73) Assignee: Amersham Biosciences Corp, Piscataway, NJ (US)

( * ) Notice: Subject to any disclaimer, the term of this patent is extended or adjusted under 35 U.S.C. 154(b) by 0 days.

(21) Appl. No.: 10/190,967

(22) Filed: Jul. 8, 2002

(65) Prior Publication Data

US 2004/0005573 A1 Jan. 8, 2004

(Under 37 CFR 1.47)

Related U.S. Application Data

(60) Provisional application No. 60/303,451, filed on Jul. 6, 2001.

(51) Int. Cl.[7] .......................... C12Q 1/68; C07H 21/04
(52) U.S. Cl. ....................... 435/6; 536/23.1; 536/24.3; 536/24.33; 530/350
(58) Field of Search .............................................. 435/6

(56) References Cited

U.S. PATENT DOCUMENTS

| | | |
|---|---|---|
| 5,210,036 A | 5/1993 | Comb et al. |
| 5,837,450 A | 11/1998 | Dahlberg et al. |
| 5,948,614 A | 9/1999 | Chatterjee |

FOREIGN PATENT DOCUMENTS

| | | |
|---|---|---|
| EP | 0 902 035 | 3/1999 |
| WO | WO94/29482 | 12/1994 |
| WO | WO98/40496 | 9/1998 |
| WO | WO99/47539 | 9/1999 |
| WO | WO99/65938 | 12/1999 |
| WO | WO01/14568 | 3/2001 |

OTHER PUBLICATIONS

Foldes–Papp, Z., et al. "Fluorescent high–density labeling of DNA: error–free substitution for a normal nucleotide" Journal of Biotechnology, Elsevier Science Publishers, Amsterdam, NL vol. 86, No. 3, Apr. 13, 2001 pp. 237–253.

Reeve, M. A., et al. "A novel thermostable polymerase for DNA Sequencing" Nature, MacMillian Journals Ltd., London, GB vol. 376, Aug. 31, 1995 pp. 796–797.

Voss, H., et al. "Automated Cycle Sequencing with Taquenase: Protocols for Internal Labeling, Dye Primer and "Doublex" Simultaneous Sequencing" Biotechniques, vol. 23, No. 2, 1997 pp. 312–318.

Bolchakova, E. V., et al. "Comparison of the Properties of Different Eubacterial DNA Polymerases and Their Use in Fluorescent DNA Sequencing" International Genome Sequencing and Analysis Conference, vol. 12, 2000, p. 50 12th International Genome Sequencing and Analysis Conference: Miami Beach, Florida, USA Sep. 12–15, 2000.

*Primary Examiner*—Jeffrey Fredman
*Assistant Examiner*—Heather G. Calamita
(74) *Attorney, Agent, or Firm*—Royal N. Ronning, Jr.; Stephen G. Ryan; Yonggang Ji

(57) ABSTRACT

Thermostable DNA polymerases both in native form and having single amino acid substitutions and optionally N-terminal deletions are disclosed. These polymerases exhibit a substantial improvement of DNA sequencing performance compared to Taq DNA polymerase. The instant DNA polymerases also possess improved salt tolerance.

5 Claims, 16 Drawing Sheets

FIGURE 1 Tth DNA Polymerase

```
  1 meamlplfep kgrvllvdgh hlayrtffal kglttsrgep vqavygfaks llkalkedgy
 61 kavfvvfdak apsfrheaye aykagraptp edfprqlali kelvdllgft rlevpgyead
121 dvlatlakka ekegyevril tadrdlyqlv sdrvavlhpe ghlitpewlw ekyglrpeqw
181 vdfralvgdp sdnlpgvkgi gektalkllk ewgslenllk nldrvkpenv rekikahled
241 lrlslelsrv rtdlplevdl aqgrepdreg lraflerlef gsllhefgll eapapleeap
301 wpppegafvg fvlsrpepmw aelkalaacr dgrvhraadp laglkdlkev rgllakdlav
361 lasregldlv pgddpmllay lldpsnttpe gvarryggew tedaahrall serlhrnllk
421 rlegeekllw lyhevekpls rvlahmeatg vrrdvaylqa lslelaeeir rleeevfrla
481 ghpfnlnsrd qlervlfdel rlpalgktqk tgkrstsaav lealreahpi vekilqhrel
541 tklkntyvdp lpslvhprtg rlhtrfnqta tatgrlsssd pnlqnipvrt plgqrirraf
601 vaeagwalva ldysqielrv lahlsgdenl irvfqegkdi htqtaswmfg vppeavdplm
661 rraaktvnfg vlygmsahrl sqelaipyee avafieryfq sfpkvrawie ktleegrkrg
721 yvetlfgrrr yvpdlnarvk svreaaerma fnmpvqgtaa dlmklamvkl fprlremgar
781 mllqvhdell leapqaraee vaalakeame kayplavple vevgmgedwl sakg
```

FIGURE 2 Tsp JS1 DNA Polymerase

```
  1 MRGMLPLFEP KGRVLLVDGH HLAYRNFFAL KGLTTSRGEP VQGVYGFAKS LLKALKEDGD
 61 VVIVVFDAKA PSFRHEAYEA YKAGRAPTPE DFPRQLALIK ELVDLLGLER LEVPGFEADD
121 VLATLAKQAE REGYEVRILT ADRDLFQLLS DRIAVLHPEG HLITPGWLWE RYGLKPEQWV
181 DFRALAGDPS DNIPGVKGIG EKTALKLLKE WGSLENLLKN LDHVKPPSVR EKILAHLDDL
241 RLSQELSRVR TDLPLKVDFK KRREPDREGL KAFLERLEFG SLLHEFGLLE SPLPAEEAPW
301 PPPEGAFLGY RLSRPEPMWA ELLALAASAK GRVYRAEEPY GALRGLKEVR GLLAKDLAVL
361 ALREGLDLPP TDDPMLLAYL LDPSNTTPEG VARRYGGEWT EEAGERAVLS ERLYENLLGR
421 LRGEEKLLWL YEEVEKPLSR VLAHMREATGV RLDVAYLKAL SLEVAEEMRR LEEEVFRLAG
481 HPFNLNSRDQ LERVLFDELG LPPIGKTEKT GKRSTSAAVL EALREAHPIV EKILQYRELA
541 KLKGTYIDPL PALVHPKTGR LHTRFNQTAT ATGRLSSSDP NLQNIPVRTP LGQRIRRAFV
601 AEEGYLLVAL DYSQIELRVL AHLSGDENLI QVFQEGRDIH TQTASWMFGL PAEAIDPLMR
661 RAAKTINFGV LYGMSAHRLS QELSIPYEEA VAFIDRYFQS YPKVKAWIER TLEEGRQRGY
721 VETLFGRRRY VPDLNARVKS VREAAERMAF NMPVQGTAAD LMKLAMVRLF PRLPEVGARM
781 LLQVHDELLL EAPKERAEAA AALAKEVMEG VWPLAVPLEV EVGIGEDWLS AKE
```

FIGURE 3 Taq DNA Polymerase

```
  1 mrgmlplfep kgrvllvdgh hlayrtfhal kglttsrgep vqavygfaks llkalkedgd
 61 avivvfdaka psfrheaygg ykagraptpe dfprqlalik elvdllglar levpgyeadd
121 vlaslakkae kegyevrilt adkdlyqlls drihvlhpeg ylitpawlwe kyglrpdqwa
181 dyraltgdes dnlpgvkgig ektarkllee wgsleallkn ldrlkpaire kilahmddlk
241 lswdlakvrt dlplevdfak rrepdrerlr aflerlefgs llhefglles pkaleeapwp
301 ppegafvgfv lsrkepmwad llalaaargg rvhrapepyk alrdlkearg llakdlsvla
361 lreglqlppg ddpmllayll dpsnttpegv arryggewte ageraalse rlfanlwgrl
421 egeerllwly reverplsav lahmeatgvr ldvaylrals levaeeiarl eaevfrlagh
481 pfnlnsrdql ervlfdelgl paigktektg krstsaavle alreahpive kilqyreltk
541 lkstyidplp dlihprtgrl htrfnqtata tgrlsssdpn lqnipvrtpl gqrirrgfia
601 eegwllvald ysqielrvla hlsgdenlir vfqegrdiht etaswmfgvp reavdplmrr
661 aaktinfgvl ygmsahrlsq elaipyeeaq afieryfqsf pkvrawiekt leegrrrgyv
721 etlfgrrryv pdlearvksv reaaermafn mpvqgtaadl mklamvklfp rleemgarml
781 lqvhdelvle apkeraeava rlakevmegv yplavpleve vgigedwlsa ke
```

FIGURE 5 Tsp JS1 Δ271/F667Y DNA Polymerase

```
  1 MLERLEFGSL LHEFGLLESP LPAEEAPWPP PEGAFLGYRL SRPEPMWAEL LALAASAKGR
 61 VYRAEEPYGA LRGLKEVRGL LAKDLAVLAL REGLDLPPTD DPMLLAYLLD PSNTTPEGVA
121 RRYGGEWTEE AGERAVLSER LYENLLGRLR GEEKLLWLYE EVEKPLSRVL AHMEATGVRL
181 DVAYLKALSL EVAEEMRRLE EEVFRLAGHP FNLNSRDQLE RVLFDELGLP PIGKTEKTGK
241 RSTSAAVLEA LREAHPIVEK ILQYRELAKL KGTYIDPLPA LVHPKTGRLH TRFNQTATAT
301 GRLSSSDPNL QNIPVRTPLG QRIRRAFVAE EGYLLVALDY SQIELRVLAH LSGDENLIQV
361 FQEGRDIHTQ TASWMFGLPA EAIDPLMRRA AKTINYGVLY GMSAHRLSQE LSIPYEEAVA
421 FIDRYFQSYP KVKAWIERTL EEGRQRGYVE TLFGRRRYVP DLNARVKSVR EAAERMAFNM
481 PVQGTAADLM KLAMVRLFPR LPEVGARMLL QVHDELLLEA PKERAEAAAA LAKEVMEGVW
541 PLAVPLEVEV GIGEDWLSAK E
```

FIGURE 6 Tsp JS1 Δ271/F667Y/E681R DNA Polymerase

```
  1 MLERLEFGSL LHEFGLLESP LPAEEAPWPP PEGAFLGYRL SRPEPMWAEL LALAASAKGR
 61 VYRAEEPYGA LRGLKEVRGL LAKDLAVLAL REGLDLPPTD DPMLLAYLLD PSNTTPEGVA
121 RRYGGEWTEE AGERAVLSER LYENLLGRLR GEEKLLWLYE EVEKPLSRVL AHMEATGVRL
181 DVAYLKALSL EVAEEMRRLE EEVFRLAGHP FNLNSRDQLE RVLFDELGLP PIGKTEKTGK
241 RSTSAAVLEA LREAHPIVEK ILQYRELAKL KGTYIDPLPA LVHPKTGRLH TRFNQTATAT
301 GRLSSSDPNL QNIPVRTPLG QRIRRAFVAE EGYLLVALDY SQIELRVLAH LSGDENLIQV
361 FQEGRDIHTQ TASWMFGLPA EAIDPLMRRA AKTINYGVLY GMSAHRLSQR LSIPYEEAVA
421 FIDRYFQSYP KVKAWIERTL EEGRQRGYVE TLFGRRRYVP DLNARVKSVR EAAERMAFNM
481 PVQGTAADLM KLAMVRLFPR LPEVGARMLL QVHDELLLEA PKERAEAAAA LAKEVMEGVW
541 PLAVPLEVEV GIGEDWLSAK E
```

FIGURE 7 Tth D18A/F667Y/E681R DNA Polymerase

```
  1 meamlplfep kgrvllvagh hlayrtffal kglttsrgep vqavygfaks llkalkedgy
 61 kavfvvfdak apsfrheaye aykagraptp edfprqlali kelvdllgft rlevpgyead
121 dvlatlakka ekegyevril tadrdlyqlv sdrvavlhpe ghlitpewlw ekyglrpeqw
181 vdfralvgdp sdnlpgvkgi gektalkllk ewgslenllk nldrvkpenv rekikahled
241 lrlslelsrv rtdlplevdl aqgrepdreg lraflerlef gsllhefgll eapapleeap
301 wpppegafvg fvlsrpepmw aelkalaacr dgrvhraadp laglkdlkev rgllakdlav
361 lasregldlv pgddpmllay lldpsnttpe gvarryggew tedaahrall serlhrnllk
421 rlegeekllw lyhevekpls rvlahmeatg vrrdvaylqa lslelaeeir rleeevfrla
481 ghpfnlnsrd qlervlfdel rlpalgktqk tgkrstsaav lealreahpi vekilqhrel
541 tklkntyvdp lpslvhprtg rlhtrfnqta tatgrlsssd pnlqnipvrt plgqrirraf
601 vaeagwalva ldysqielrv lahlsgdenl irvfqegkdi htqtaswmfg vppeavdplm
661 rraaktvnyg vlygmsahrl sqrlaipyee avafieryfq sfpkvrawie ktleegrkrg
721 yvetlfgrrr yvpdlnarvk svreaaerma fnmpvqgtaa dlmklamvkl fprlremgar
781 mllqvhdell leapqaraee vaalakeame kayplavple vevgmgedwl sakg
```

FIGURE 8 Tth Δ271/F667Y/E681R DNA Polymerase

```
  1 mlerlefgsl lhefglleap apleeapwpp pegafvgfvl srpepmwael kalaacrdgr
 61 vhraadplag lkdlkevrgl lakdlavlas regldlvpgd dpmllaylld psnttpegva
121 rryggewted aahrallser lhrnllkrle geekllwlyh evekplsrvl ahmeatgvrr
181 dvaylqalsl elaeeirrle eevfrlaghp fnlnsrdqle rvlfdelrlp algktqktgk
241 rstsaavlea lreahpivek ilqhreltkl kntyvdplps lvhprtgrlh trfnqtatat
301 grlsssdpnl qnipvrtplg qrirrafvae agwalvaldy sqielrvlah lsgdenlirv
361 fqegkdihtq taswmfgvpp eavdplmrra aktvnygvly gmsahrlsqr laipyeeava
421 fieryfqsfp kvrawiektl eegrkrgyve tlfgrrryvp dlnarvksvr eaaermafnm
481 pvqgtaadlm klamvklfpr lremgarmll qvhdelllea pqaraeevaa lakeamekay
541 plavplevev gmgedwlsak g
```

FIGURE 9 Nucleotide Sequence of TspJS1 DNA Polymerase gene

```
   1 ATGAGAGGCA TGCTTCCACT TTTTGAGCCC AAGGGCCGGG TCCTCCTGGT GGACGGCCAC
  61 CACCTGGCCT ACCGCAACTT TTTCGCCCTC AAAGGGCTCA CCACGAGCCG GGGCGAGCCG
 121 GTGCAAGGGG TCTACGGCTT CGCCAAAAGC CTCCTCAAGG CCCTGAAGGA GGACGGGGAC
 181 GTGGTCATCG TGGTCTTTGA CGCCAAGGCC CCCTCTTTCC GCCACGAGGC CTACGAGGCC
 241 TACAAGGCGG GCCGGCCCC CACCCCGGAG GACTTTCCCC GGCAGCTCGC CCTCATAAAG
 301 GAGCTGGTGG ACCTCTTGGG GCTGGAGCGC CTCGAGGTCC CGGGCTTTGA AGCGGACGAT
 361 GTCCTCGCCA CCTTGGCCAA GCAAGCGGAG CGGGAAGGGT ACGAGGTGCG CATCCTCACC
 421 GCCGACCGGG ACCTCTTCCA GCTCCTTTCG GACCGCATCG CCGTCCTCCA CCCGGAAGGG
 481 CACCTCATCA CCCCGGGGTG GCTTTGGGAG CGGTACGGTC TGAAGCCGGA GCAGTGGGTG
 541 GACTTCCGCG CCCTGGCCGG CGACCCCTCC GACAACATCC CCGGGGTGAA GGGAATCGGG
 601 GAGAAGACCG CCCTGAAGCT CCTCAAGGAG TGGGGGAGCC TGGAAAACCT CCTCAAGAAC
 661 CTGGACCATG TGAAGCCTCC TTCCGTAAGG GAGAAGATCC TCGCCCACCT GGACGACCTC
 721 AGGCTCTCCC AGGAGCTTTC CCGGGTGCGC ACGGACCTCC CCTTGAAGGT GGACTTTAAA
 781 AAGCGGCGGG AGCCCGATAG GGAAGGGCTT AAGGCCTTCT GGAGCGGCT TGAGTTTGGA
 841 AGCCTCCTCC ACGAGTTCGG CCTCCTGGAA AGCCCCCTTC CGGCGGAGGA GGCCCCATGG
 901 CCGCCGCCGG AAGGGGCCTT TTTGGGCTAC CGCCTTTCCC GGCCCGAGCC CATGTGGGCG
 961 GAGCTTCTTG CCTTGGCGGC GAGCGCCAAG GGCCGGGTTT ACCGGCGCGGA GGAGCCCTAT
1021 GGGGCCCTAA GGGGCCTGAA GGAGGTGCGG GGGCTTCTTG CCAAGGACCT CGCCGTCTTG
1081 GCCCTAAGGG AGGGCCTGGA CCTTCCCCCC ACGGACGACC CCATGCTCCT CGCTTACCTC
1141 CTGGACCCCT CCAACACCAC CCCCGAGGGC GTGGCCCGGC GGTATGGGGG GGAGTGGACG
1201 GAGGAGGCGG GGGAGCGGGC GGTGCTTTCC GAAAGGCTCT ACGAGAACCT CCTTGGGCGC
1261 TTGAGAGGGG AAGAGAAGCT CCTTTGGCTT TACGAGGAGG TGGAAAAGCC CCTCTCCCGG
1321 GTCCTCGCCC ACATGGAGGC CACGGGGGTG AGGCTGGACG TGGCCTACCT CAAGGCCCTT
1381 TCCCTGGAGG TGGCGGAGGA GATGCGCCGC CTGGAGGAGG AGGTCTTCCG CCTGGCGGGC
1441 CACCCCTTCA ACCTCAATTC CCGCGACCAG CTGGAAAGGG TGCTCTTTGA CGAGCTCGGC
1501 CTTCCCCCCA TCGGCAAGAC GGAGAAGACT GGGAAGCGCT CCACGAGCGC CGCCGTCCTC
1561 GAGGCCCTGC GGGAGGCCCA CCCCATCGTG GAAAAGATCC TTCAGTACCG GGAACTGGCC
1621 AAGCTCAAGG GCACCTACAT TGACCCCCTT CCCGCCCTGG TCCACCCCAA GACGGGGCGG
1681 CTCCACACCC GCTTCAACCA GACGGCCACG GCCACGGGCC GCCTTTCCAG CTCCGACCCC
1741 AACCTGCAGA ACATCCCCGT GCGCACCCCC TTGGGCCAAA GGATCCGCCG GGCCTTCGTG
1801 GCCGAGGAGG GGTACCTGCT CGTGGCCCTG GACTATAGCC AGATTGAGCT CAGGGTCCTG
1861 GCCCACCTCT CGGGGGACGA GAACCTCATC CAGGTCTTCC AGGAGGGCCG GGACATCCAC
1921 ACCCAGACGG CGAGCTGGAT GTTCGGCCTG CCGGCGGAGG CCATAGACCC CCTCATGCGC
1981 CGGGCGGCCA AGACCATCAA CTTCGGCGTC CTTTACGGCA TGTCCGCCCA TCGGCTTTCC
2041 CAAGAGCTCA GCATCCCCTA CGAGGAGGCG GTGGCCTTCA TTGACCGCTA TTTCCAGAGC
2101 TACCCCAAGG TGAAGGCCTG GATTGAAAGG ACCCTGGAGG AGGGGCGGCA GAGGGGGTAT
2161 GTGGAAACCC TCTTCGGCCG CAGGCGCTAC GTGCCCGACC TCAACGCCCG GGTAAAGAGC
2221 GTGCGGGAGG CGGCGGAGCG CATGGCCTTT AACATGCCCG TGCAGGGCAC CGCCGCCGAC
2281 CTGATGAAGC TCGCCATGGT GAGGCTTTTC CCCAGGCTTC CGAGGTGGG GGCGCGGATG
2341 CTCCTCCAGG TGCACGACGA GCTCCTCCTG GAGGCGCCCA AGGAGCGGGC GGAGGCGGCG
2401 GCGGCCCTGG CCAAGGAGGT CATGGAGGGG GTCTGGCCCC TGGCCGTGCC CCTGGAGGTG
2461 GAGGTGGGGA TAGGGGAGGA CTGGCTCTCC GCCAAGGAGT GA
```

```
Tsp  MRGMLPLFEPKGRVLLVDGHHLAYRNFFALKGLTTSRGEPVQGVYGFAKSLLKALKEDG-   59
Taq  MRGMLPLFEPKGRVLLVDGHHLAYRTFHALKGLTTSRGEPVQAVYGFAKSLLKALKEDG-   59
Tth  MEAMLPLFEPKGRVLLVDGHHLAYRTFFALKGLTTSRGEPVQAVYGFAKSLLKALKEDGY   60
Tca  MEAMLPLFEPKGRVLLVDGHHLAYRTFFALKGLTTSRGEPVQAVYGFAKSLLKALKEDGY   60
Tfl  M-AMLPLFEPKGRVLLVDGHHLAYRTFFALKGLTTSRGEPVQAVYGFAKSLLKALKEDG-   58
Tos  MKAMLPLFEPKGRVLLVDGHHLAYRTFFALKGLTTSRGEPVQAVYGFAKSLLKALKEDGY   60
Tfi  MTPLFDLEEPKRVLLVDGHHLAYRTFYAL-SLTTSRGEPVQMVYGFARSLLKALKEDG-   58

Tsp  DVVIVVFDAKAPSFRHEAYEAYKAGRAPTPEDFPRQLALIKELVDLLGLERLEVPGFEAD  119
Taq  DAVIVVFDAKAPSFRHEAYGGYKAGRAPTPEDFPRQLALIKELVDLLGLARLEVPGYEAD  119
Tth  KAVFVVFDAKAPSFRHEAYEAYKAGRAPTPEDFPRQLALIKELVDLLGFTRLEVPGYEAD  120
Tca  KAVFVVFDAKAPSFRHEAYEAYKAGRAPTPEDFPRQLALIKELVDLLGFTRLEVPGYEAD  120
Tfl  DVVVVVFDAKAPSFRHEAYEAYKAGRAPTPEDFPRQLALIKELVDLLGVRLEVPGFEAD   118
Tos  KAVFVVFDAKAPSFRHEAYEAYKAGRAPTPEDFPRQLALIKELVDLLGFTRLEVPGFEAD  120
Tfi  QAVVVVFDAKAPSFRHEAYEAYKAGRAPTPEDFPRQLALVKRLVDLLGLVRLEAPGYEAD  118

Tsp  DVLATLAKQAEREGYEVRILTADRDLFQLLSDRIAVLHPEGHLITPGWLWERYGLKPEQW  179
Taq  DVLASLAKKAEKEGYEVRILTADKDLYQLLSDRIHVLHPEGYLITPAWLWEKYGLRPDQW  179
Tth  DVLATLAEKEGYEVRILTADRDLYQLVSDRVAVLHPEGHLITPEWLWEKYGLRPEQW    180
Tca  DVLATLAKNPEKEGYEVRILTADRDLDQLVSDRVAVLHPEGHLITPEWLWQKYGLKPEQW  180
Tfl  DVLATLAKRAEKEGYEVRILTADRDLYQLLSERIAILHPEGYLITPAWLYEKYGLRPEQW  178
Tos  DVLAKKAERGYEVRILTADRDLYQLVSDRVAVLHPEGHLITPEWLWEKYGLKPEQW     180
Tfi  DVLGTLAKKAEREGMEVRILTGDRDFFQLLSEKVSVLLPDGTLVTPKDVQEKYGVPPERW 178
```

FIGURE 17

```
Tsp  VDFRALAGDPSDNIPGVKGIGEKTALKLLKEWGSLENLLKNLDHVKPPSVREKILAHLDD  239
Taq  ADYRALTGDESDNLPGVKGIGEKTARKLLEEWGSLEALLKNLDRLKPA-IREKILAHMDD  238
Tth  VDFRALVGDPSDNLPGVKGIGEKTALKLLKEWGSLENLLKNLDRVKPENVREKIKAHLED  240
Tca  VDFRALVGDPSDNLPGVKGIGEKTALKLLKEWGSLENLLKNLDRVKPENVREKIKAHLED  240
Tfl  VDYRALAGDPSDNIPGVKGIGEKTAQRLIREWGSLENLFQHLDQVKP-SLREKLQAGMEA  237
Tca  VDFRALVGDPSDNLPGVKGIGEKTALKLLKEWGSLENILKNLDRVKPESVRERIKAHLED  240
Tfi  VDFRALTGDRSDNIPGVAGIGEKTALRLILAEWGSVENLLKNLDRVKPDSLRRKIEAHLED  238

Tsp  LRLSQELSRVRTDLPLKVDFK--KRREPDREGLKAFLERLEFGSLLHEFGLLESPLPAEE  297
Taq  LKLSWDLAKVRTDLPLEVDFA--KRREPDRERLRAFLERLEFGSLLHEFGLLESPKALEE  296
Tth  LRLSLELSRVRTDLPLEVDLA--QGREPDREGLRAFLERLEFGSLLHEFGLLEAPAPLEE  298
Tca  LRLSLELSRVRTDLPLEVDLA--QGREPDREGLRAFLERLEFGSLLHEFGLLEAPAPLEE  298
Tfl  LALSRKLSQVHTDLPLEVDFG--RRRTPNLEGLRAFLERLEFGSLLHEFGLLEGPKAAEE  295
Tca  LKLSLELSRVRSDLPLEVDFA--RRREPDREGLRAFLERLEFGSLLHEFGLLEAPAPLEE  298
Tfi  LHLSLDLARIRTDLPLEVDFKALRRTPDLEGLRAFLEELEFGSLLHEFGLLGGEKPREE  298

Tsp  APWPPPEGAFLGYRLSRPEPMWAELLALAAAKGRVYRAEEPYGALRGLKEVRGLLAKDL  357
Taq  APWPPPEGAFVGFVGFVLSRKEPMWAADLLALAAAARGGRVHRAPEPYKALRDLKEARGLLAKDL  356
Tth  APWPPPEGAFVGFVLSRKEPMWAELKALAACRDGRVHRAADPLAGLKDLKEVRGLLAKDL  358
Tca  APWPPPEGAFVGFVLSRKEPMWAELKALAACRDGRVHRAADPLAGLKDLKEVRGLLAKDL  358
Tfl  APWPPPEGAFLGFSFSRPEPMWAELLALAGAWEGRLHRAQDPLRGLRDLKGVRGILAKDL  355
Tos  APWPPPEGAFVGFVLSRPEPMWAELKALAACKEGRVHRAKDPLAGLKDLKEVRGLLAKDL  358
Tfi  APWPPPEGAFVGFLLSRKEPMWAELLALAAASEGRVHRATSPVEALADLKEARGFLAKDL  358
```

FIGURE 17 – Continued

```
Tsp  AVLALREGLDLPPTDDPMLLAYLLDPSNTTPEGVARRYGGEWTEEAGERAVLSERLYENL  417
Taq  SVLALREGLGLPPGDDPMLLAYLLDPSNTTPEGVARRYGGEWTEEAGERAALSERLFANL  416
Tth  AVLASREGLDLVPGDDPMLLAYLLDPSNTTPEGVARRYGGEWTEDAAHRALLSERLHRNL  418
Tca  AVLASREGLDLVPGDDPMLLAYLLDPSNTTPEGVARRYGGEWTEDAAHRALLSERLHRNL  418
Tfl  AVLALREGLDLFPEDDPMLLAYLLDPSNTTPEGVARRYGGEWTEDAGERALLAERLFQTL  415
Tos  AVLALREGLDLAPSDDPMLLAYLLDPSNTTPEGVARRYGGEWTEDAAHRALLAERLQQNL  418
Tfi  AVLALREGVALDPTDDPLLVAYLLDPANTHPEGVARRYGGEFTEDAAERALLSERLFQNL  418

Tsp  LGRLRGEEKLLWLYEEVEKPLSRVLAHMEATGVRLDVAYLKALSLEVAEEMRRLEEEVFR  477
Taq  WGRLEGEERLLWLYREVERPLSAVLAHMEATGVRLDVAYLRALSLEVAEEIARLEAEVFR  476
Tth  LKRLEGEEKLLWLYHEVEKPLSRVLAHMEATGVRRDVAYLQALSLELAEEIRRLEEEVFR  478
Tca  LKRLQGEEKLLWLYHEVEEKPLSRVLAHMEATGVRLDVAYLQALSLELAEEIRRLEEEVFR  478
Tfl  KERLKGEERLLWLYEEVEKPLSRVLARMEATGVRLDVAYLQALSLEVAEVRQLEEEVFR  475
Tos  LERLKGEEKLLWLYQEVEKPLSRVLAHMEATGVRLDVAYLKALSLELAEEIRRLEEEVFR  478
Tfi  FPRLS--EKLLWLYQEVERPLSRVLAHMEARGVRLDVPLLEALSFELEKEMERLEGEVFR  476

Tsp  LAGHPFNLNSRDQLERVLFDELGLPPIGKTEKTGKRSTSAAVLEALREAHPIVEKILQYR  537
Taq  LAGHPFNLNSRDQLERVLFDELGLPAIGKTEKTGKRSTSAAVLEALREAHPIVEKILQYR  536
Tth  LAGHPFNLNSRDQLERVLFDELRLRLPALGKTQKTGKRSTSAAVLEALREAHPIVEKILQHR  538
Tca  LAGHPFNLNSRDQLERVLFDELRLRLPALGKTQKTGKRSTSAAVLEALREAHPIVEKILQHR  538
Tfl  LAGHPFNLNSRDQLERVLFDELGLPAIGKTEKTGKRSTSAAVLEALREAHPIVDRILQYR  535
Tos  LAGHPFNLNSRDQLERVLFDELRLRLPALGKTQKTGKRSTSAAVLEALREAHPIVEKILQHR  538
Tfi  LAGHPFNLNSRDQLERVLFDELGLTPVGRTEKTGKRSTAQGALEALRGAHPIVELILQYR  536
```

FIGURE 17 — Continued

```
Tsp  ELAKLKGTYIDPLPLPALVHPKTGRLHTRFNQTATATGRLSSSSDPNLQNIPVRTPLGQRIRR  597
Taq  ELTKLKSTYIDPLPDLIHPRTGRLHTRFNQTATATGRLSSSSDPNLQNIPVRTPLGQRIRR  596
Tth  ELTKLKNTYVDPLPSLVHPRTGRLHTRFNQTATATGRLSSSSDPNLQNIPVRTPLGQRIRR  598
Tca  ELTKLKNTYVDPLPSLVHPNTGRLHTRFNQTATATGRLSSSSDPNLQNIPVRTPLGQRIRR  598
Tfl  ELTKLKNTYIDPLPALVHPKTGRLHTRFNQTATATGRLSSSSDPNLQNIPVRTPLGQRIRR  595
Tos  ELTKLKNTYVDPLPGLVHPRTGRLHTRFNQTATATGRLSSSSDPNLQNIPIRTPLGQRIRR  598
Tfi  ELSKLKSTYLDPLPRLVHPRTGRLHTRFNQTATATGRLSSSSDPNLQNIPVRTPLGQRIRK  596

Tsp  AFVAEEGYLLVALDYSQIELRVLAHLSGDENLIQVFQEGRDIHTQTASWMFGLPAEAIDP   657
Taq  GFIAEEGWLLVALDYSQIELRVLAHLSGDENLIRVFQEGRDIHTETASWMFGVPREAVDP   656
Tth  AFVAEAGWALVALDYSQIELRVLAHLSGDENLIRVFQEGKDIHTQTASWMFGVPPEAVDP   658
Tca  AFVAEAGWALVALDYSQIELRVLAHLSGDENLIRVFQEGKDIHTQTASWMFGVPPEAVDP   658
Tfl  AFVAEEGWVLVVLDYSQIELRVLAHLSGDENLIRVFQEGRDIHTQTASWMFGVSPEGVDP   655
Tos  AFVAEAGWALVALDYSQIELRVLAHLSGDENLIRVFQEGKDIHTQTASWMFGVSPEAVDP   658
Tfi  AFVAEEGWLLLAADYSQIELRVLAHLSGDENLKRVFREGKDIHTETAAWMFGLDPALVDP   656

Tsp  LMRRAAKTINFGVLYGMSAHRLSQELSIPYEEAVAFIDRYFQSYPKVKAWIERTLEEGRQ   717
Taq  LMRRAAKTINFGVLYGMSAHRLSQELAIPYEEAQAFIERYFQSFPKVRAWIEKTLEEGRR   716
Tth  LMRRAAKTVNFGVLYGMSAHRLSQELAIPYEEAVAFIERYFQSFPKVRAWIEKTLEEGRK   718
Tca  LMRRAAKTVNFGVLYGMSAHRLSQELAIPYEEAVAFIERYFQSFPKVRAWIEKTLEEGRK   718
Tfl  LMRRAAKTINFGVLYGMSAHRLSGELSIPYEEAVAFIERYFQSYPKVRAWIEGTLEEGRR   715
Tos  LMRRAAKTVNFGVLYGMSAHRLSQELAIPYEEAVAFIERYFQSFPKVRAWIEKTLEEGRK   718
Tfi  KMRRAAKTVNFGVLYGMSAHRLSQELGIDYKEAEAFIERYFQSFPKVRAWIERTLEEGRT   716
```

FIGURE 17 – Continued

```
Tsp  RGYVETLFGRRRYVPDLNARVKSVREAAERMAFNMPVQGTAADLMKLAMVRLFPRLPEVG  777
Taq  RGYVETLFGRRRYVPDLEARVKSVREAAERMAFNMPVQGTAADLMKLAMVKLFPRLEEMG  776
Tth  RGYVETLFGRRRYVPDLNARVKSVREAAERMAFNMPVQGTAADLMKLAMVKLFPRLREMG  778
Tca  RGYVETLFGRRRYVPDLNARVKSVREAAERMAFNMPVQGTAADLMKLAMVKLFPRLREMG  778
Tfl  RGYVETLFGRRRYVPDLNARVKSVREAAERMAFNMPVQGTAADLMKLAMVRLFPRLQELG  775
Tos  RGYVETLFGRRRYVPDLNARVKSVREAAERMAFNMPVQGTAADLMKLAMVKLFPHLREMG  778
Tfi  RGYVETLFGRRRYVPDLASRVRSVREAAERMAFNMPVQGTAADLMKLAMVKLFPRLKPLG  776

Tsp  ARMLLQVHDELLLEAPKERAEAAAALAKEVMEGVWPLAVPLEVEVGIGEDWLSAK-E     833
Taq  ARMLLQVHDELVLEAPKERAEAAAALAKEVMEGVYPLAVPLEVEVGIGEDWLSAK-E     832
Tth  ARMLLQVHDELLLEAPQARAEEVAALAKEAMEKAYPLAVPLEVEVGMGEDWLSAK-G     834
Tca  ARMLLQVHDELLLEAPQAGAEEVAALAKEAMEKAYPLAVPLEVEVGMGEDWLSAK-G     834
Tfl  ARMLLQVHDELVLEAPKDRAERVAALAKEVMEGVWPLQVPLEVEVGLGEDWLSAK-E     831
Tos  ARMLLQVHDELLLEAPQARAEEVAALAKEAMEKAYPLAVPLEVEVGIGEDWLSAK-G     834
Tfi  AHLLLQVHDELVLEVPEDRAEEAKALVKEVMENAYPLDVPLEVEVGVGRDWLEAKQD     833
```

FIGURE 17 — Continued

DNA POLYMERASES HAVING AMINO ACID SUBSTITUTIONS AND HOMOLOGS THEREOF

This application claims the benefit of Provisional Application No. 60/303,451, filed Jul. 06, 2001.

BACKGROUND OF THE INVENTION

1. Field of the Invention

The instant disclosure pertains to thermostable DNA polymerases which exhibit improved robustness and efficiency. In particular, the DNA polymerases have been shown to result in a substantial improvements in desirable properties as compared to the native DNA polymerases when used in DNA sequencing reactions.

2. Background

DNA polymerases are enzymes which are useful in many recombinant DNA techniques such as nucleic acid amplification by the polymerase chain reaction ("PCR"), self-sustained sequence replication ("3 SR"), and DNA sequencing. Thermostable DNA polymerases are particularly useful. Because heat does not destroy the polymerase activity, there is no need to add additional polymerase after every denaturation step.

Naturally occurring DNA polymerases preferentially incorporate unlabeled nucleotides over corresponding labeled nucleotides into polynucleotides. This ability of DNA polymerases to discriminate against fluorescently labeled nucleotides had an undesirable effect on many molecular biology procedures that require the enzymatic addition of labeled nucleotides, e.g., labeled dideoxy terminator sequencing. Ambiguous sequencing determinations often result from the disproportionate number of labeled and unlabeled dideoxy terminators and nucleotides. On an electropherogram obtained from a capillary electrophoresis sequencing unit, this phenomena shows up as uneven peaks. Large signals due to a larger amount of incorporated labeled ddNTP can obscure smaller signals and lead to ambiguous sequence determinations. Additionally, many of the enzymes presently available are sensitive to high salt environments.

Thus, a need continues to exist for an improved DNA polymerase having improved discrimination properties (and thus resulting in improved signal uniformity) and increased tolerance to high salt conditions. These and other concerns are addressed in greater detail below.

BRIEF SUMMARY OF THE INVENTION

The instant disclosure teaches purified recombinant thermostable DNA polymerases comprising the amino acid sequences set forth in FIGS. 2, 5 and 6. The instant disclosure also teaches an isolated nucleic acid sequences that encodes such thermostable DNA polymerases, wherein said nucleic acid sequences consist of or contain of the nucleotide sequences set forth in FIG. 9, as well as a recombinant DNA vector that comprises the nucleic acid sequence, and a recombinant host cell transformed with the recombinant vector.

BRIEF DESCRIPTION OF THE FIGURES

FIG. 1 depicts the amino acid sequence (SEQ ID NO: 1) of Tth DNA polymerase (Genbank accession P52028).

FIG. 2 depicts the amino acid sequence (SEQ ID NO: 2) deduced from the DNA sequence of Tsp JS1 DNA polymerase.

FIG. 3 depicts the amino acid sequence (SEQ ID NO: 3) of Taq DNA polymerase (Genbank accession 1TAU A).

FIG. 5 depicts the amino acid sequence (SEQ ID NO: 4) of Tsp JS1 Δ271/F667Y DNA polymerase.

FIG. 6 depicts the amino acid sequence (SEQ ID NO: 5) of Tsp JS1 Δ271/F667Y/E681R DNA polymerase.

FIG. 7 depicts the amino acid sequence (SEQ ID NO: 6) of Tth D18A/F667Y/E681R DNA polymerase.

FIG. 8 depicts the amino acid sequence (SEQ ID NO: 7) of Tth Δ271/F667Y/E681R DNA polymerase.

FIG. 9 depicts the nucleotide sequence (SEQ ID NO: 8) of the gene for Tsp JS1 DNA polymerase.

FIG. 11 depicts the result of a sequencing experiment (SEQ ID NO: 9) using DYEnamic ET terminators (Amersham Biosciences) and bacteriophage M13mp18 template DNA using Tsp Δ271/F667Y DNA polymerase. The extension reactions were run in buffer that included 50 mM Tris pH 9.5, and 5 mM $MgCl_2$.

FIG. 12 depicts the result of a sequencing experiment (SEQ ID NO: 10) using DYEnamic ET terminators (Amersham Biosciences) and bacteriophage M13mp18 template DNA using Tsp Δ271/F667Y/E681R DNA polymerase. The extension reactions were run in buffer that included 50 mM Tris pH 9.5, and 5 mM $MgCl_2$.

FIG. 13 depicts the result of a sequencing experiment (SEQ ID NO: 11) using DYEnamic ET terminators (Amersham Biosciences) and bacteriophage M13mp18 template DNA using Tsp Δ271/F667Y DNA polymerase. The extension reactions were run in buffer that included 50 mM Tris pH 9.5, 5 mM $MgCl_2$.

FIG. 14 depicts the result of a sequencing experiment (SEQ ID NO: 12) using DYEnamic ET terminators (Amersham Biosciences) and bacteriophage M13mp18 template DNA using Tsp Δ271/F667Y/E681R DNA polymerase. The extension reactions were run in buffer that included 50 mM Tris pH 9.5, 5 mM $MgCl_2$.

FIG. 15 depicts the result of a sequencing experiment (SEQ ID NO: 13) using DYEnamic ET terminators (Amersham Biosciences) and bacteriophage M13mp18 template DNA using Tsp Δ271/F667Y DNA polymerase. The extension reactions were run in buffer that included 50 mM Tris pH 8.0, 5 mM $MgCl_2$ and 17.5% (v/v) glycerol.

FIG. 16 depicts the result of a sequencing experiment (SEQ ID NO: 14) using DYEnamic ET terminators (Amersham Biosciences) and bacteriophage M13mp18 template DNA using Tsp Δ271/F667Y/E681R DNA polymerase. The extension reactions were run in buffer that included 50 mM Tris pH 8.0, 5 mM $MgCl_2$ and 17.5% (v/v) glycerol.

FIG. 17 depicts an alignment of the amino acid sequences (SEQ ID NOS 2, 3, 1, 15–18, respectively, in order of appearance) of DNA polymerases from various *Thermus* species. The alignments were made using the Clustal algorithm and the PAM 100 similarity matrix. The polymerases included were: Tth (*T. thermophilus* Genbank accession P52028), Tca (*T. caldophilus* Genbank accession P80194), Taq (*T. aquaticus* Genbank accession 1TAU A), Tfl (*T. flavus* Genbank accession P30313), Tfi (*T. filiformis* Genbank accession O52225), Tos (Tsp SPS17, now called *T. oshimai* Genbank accession AAA94380), and the polymerase from Tsp JS1.

DETAILED DESCRIPTION

One objective of the instant disclosure is to increase the uniformity of dye-terminator incorporation in fluorescent dye DNA sequencing. One important DNA polymerase is Tth DNA polymerase isolated from the thermophilic bacterium *Thermus thermophilus*, the amino acid sequence for which is shown at FIG. 1. Another DNA polymerase was found in an uncharacterized thermophylic bacterium we have designated Tsp JS1. This DNA polymerase was found to have the sequence shown in FIG. 2. To eliminate 5' to 3' exonuclease activity and to provide a polypeptide more stable to proteolysis and heat treatment the N-terminus of the polymerases can be truncated, removing approximately 271 amino acids. One such truncated enzyme Taq Δ271/F272M/F667Y DNA polymerase, which is commercially available from Amersham Biosciences is known as Thermo Sequenase® DNA polymerase. Position 1 (amino acid Met) in Taq Δ271/F272M/F667Y DNA polymerase corresponds to position 272 in full length Taq polymerase. It should be noted that the numbering used in the instant disclosure is that for full-length Taq polymerase, the sequence of which is shown in FIG. 3.

Single amino acid substitutions were introduced into full-length or truncated polymerases as described (Davis, Fuller, Mamone & Huang WO 99/65938 incorporated herein by reference). These substitutions are designated as D18A, F667Y, E681R, E681M, E681H or E681W to describe the amino acid substitutions using the numbering corresponding to positions in Taq polymerase. Each of the substituted polymerases was expressed, purified, and analyzed for uniformity of dye-terminator incorporation in fluorescent sequencing studies, as assayed by signal uniformity (Davis, Nelson, Kumar, Finn, Nampalli, Flick WO 01/14568). The E681R substitution was found to result in a substantial improvement of signal uniformity compared to the native DNA polymerases. This, combined with the high stability make this polymerase an excellent choice for DNA sequencing purposes.

The polymerases may be used to generate fluorescently labeled polynucleotides by using primed templates, which templates may be used in chain termination sequencing or PCR as well understood by those skilled in the art and are described in WO 99/65938 previously incorporated herein by reference and U.S. Pat. No. 5,210,036, incorporated herein by reference.

The following examples are for illustration purposes only and should not be used in any way to limit the appended claims.

EXAMPLES

The following examples illustrate certain preferred embodiments of the invention but are not intended to be illustrative of all embodiments.

1) Example 1

Figure 4:
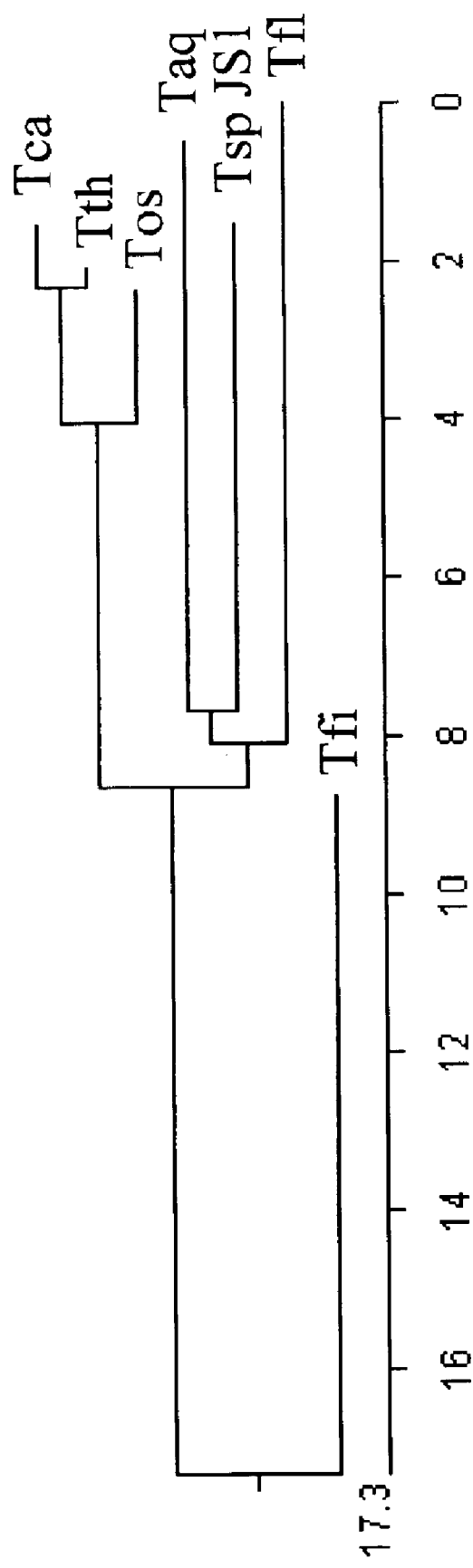
FIG. 4 depicts a phylogenetic comparison based on amino acid sequence alignment (FIG. 17) of DNA polymerases from various *Thermus* species with the polymerase of Tsp JS1.
Figure 10:
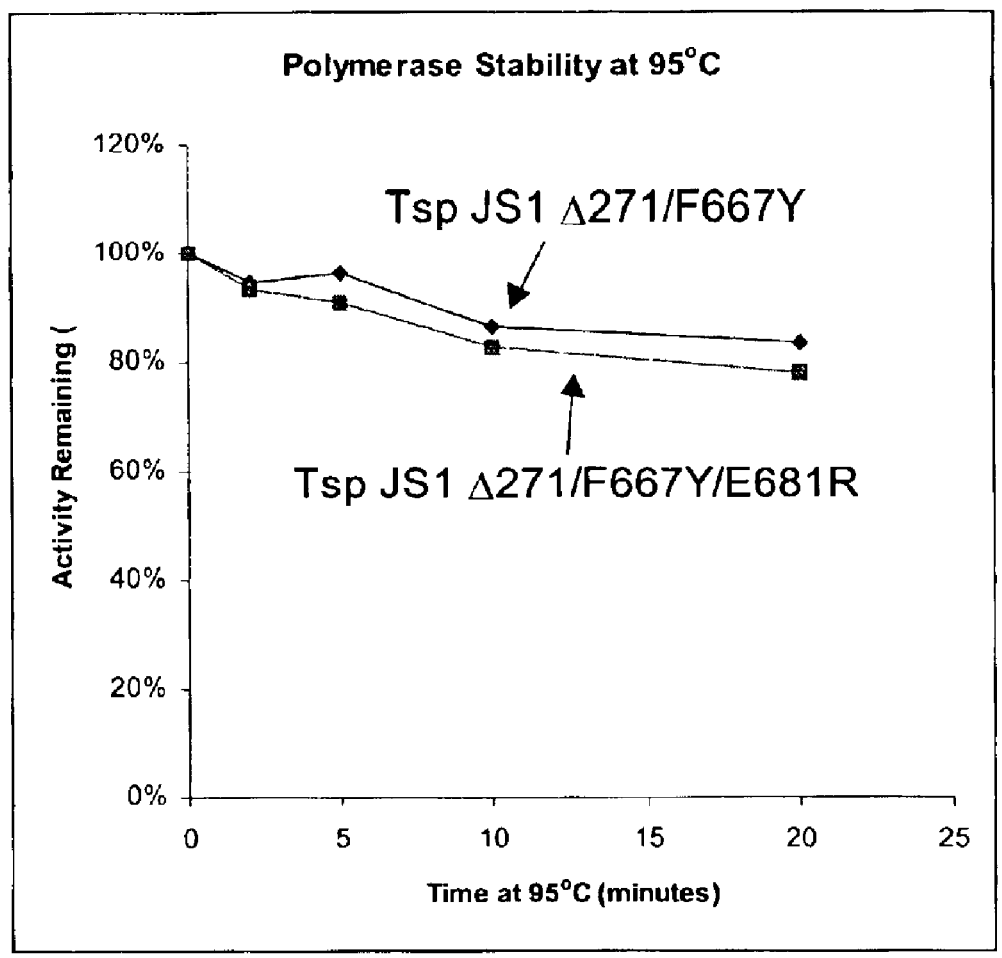
FIG. 10 depicts the stability of Tsp Δ271/F667Y and Tsp Δ271/F667Y/E681R DNA polymerases at 95° C. The DNA polymerase (approximately 2 units/$\mu$l) was incubated at 95° C. in 50 mM Tris pH 8.0, 10% glycerol, 35 mM KCl, and 1 mM $MgCl_2$ for the times indicated. Polymerase activity was then determined using the standard assay.
Figure 11:
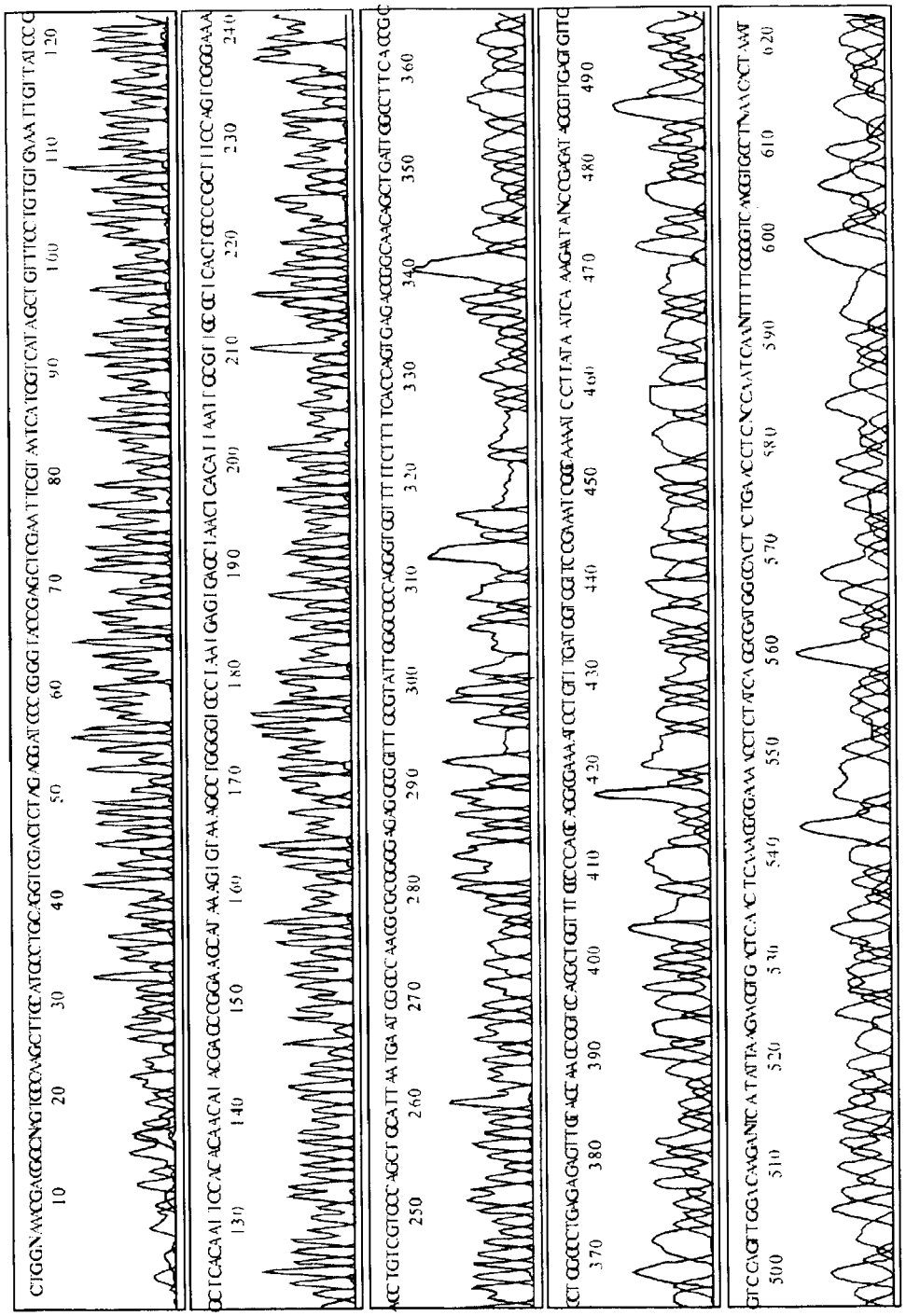
FIGS. 11–16 DNA sequencing experiments using polymerases from Tsp JS1 were performed using the DYEnamic ET terminator dye-labeled dideoxynucleotides (Amersham Biosciences). All nucleotides were used at standard concentrations, and polymerase was present at a concentration of 0.5–1.0 units/$\mu$l. Reactions were cycled 25 times at 95° C. for 30 sec., 45° C. for 15 sec. and 60° C. for 240 sec.
Figure 12:
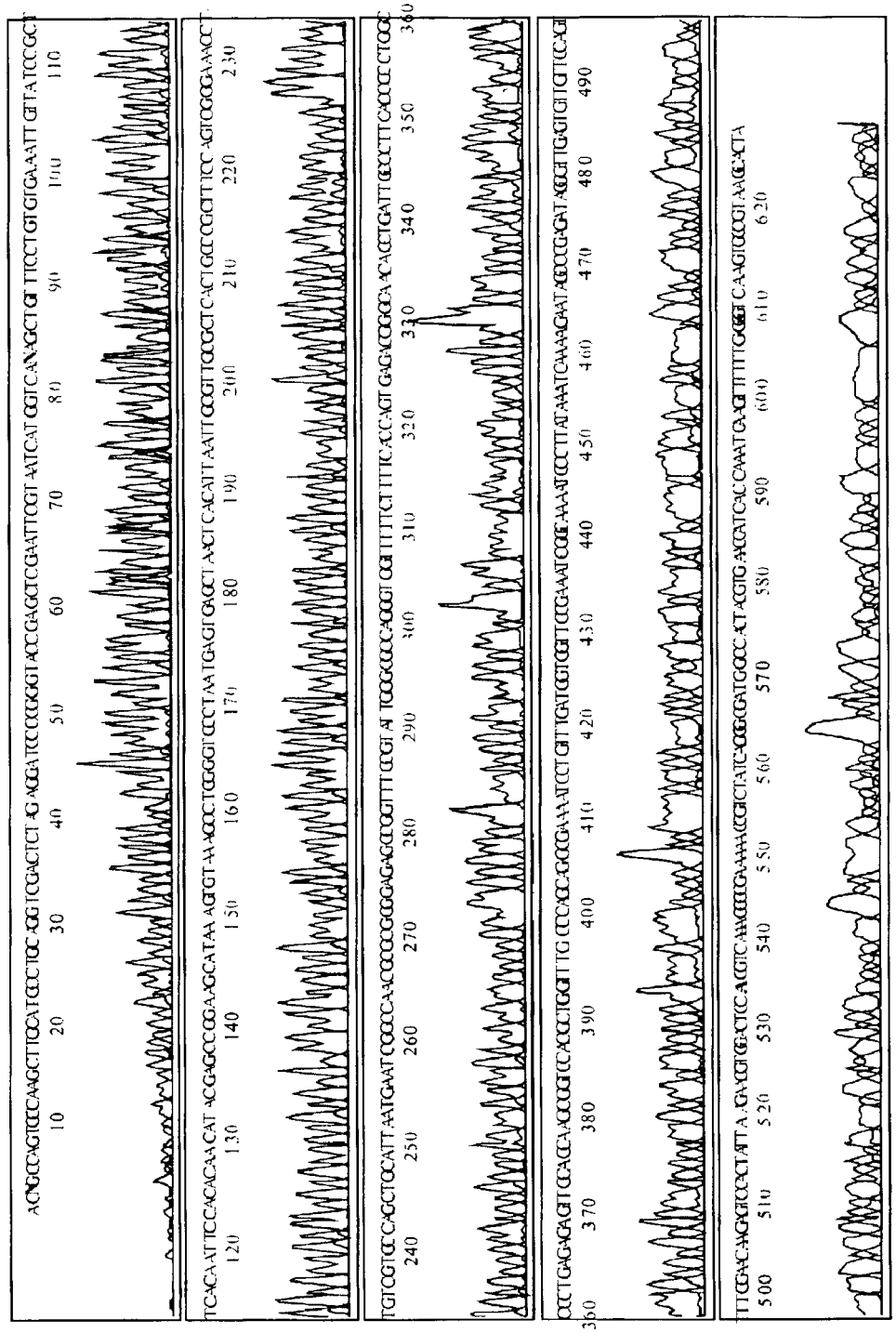
Figure 13:
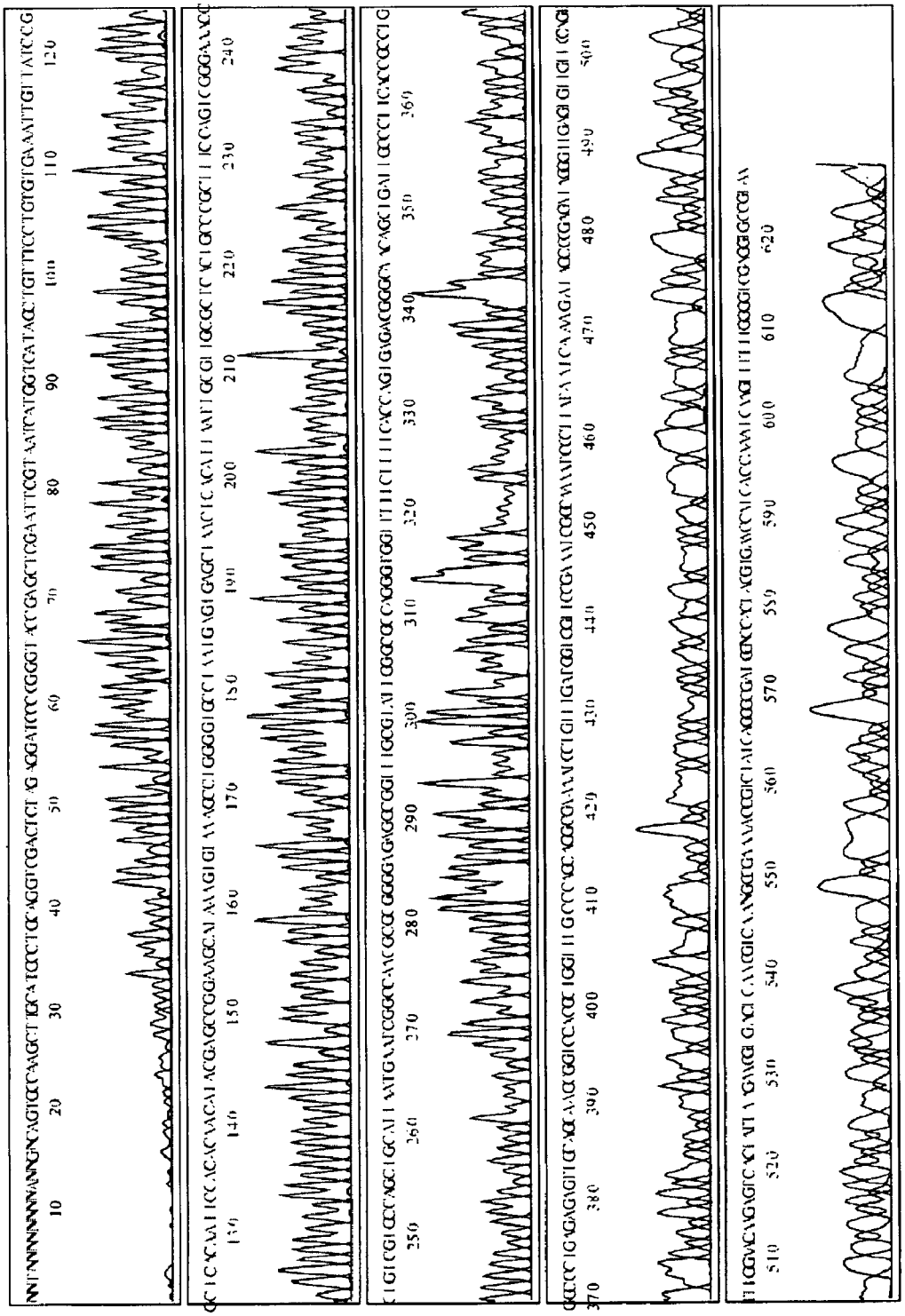
Figure 14:
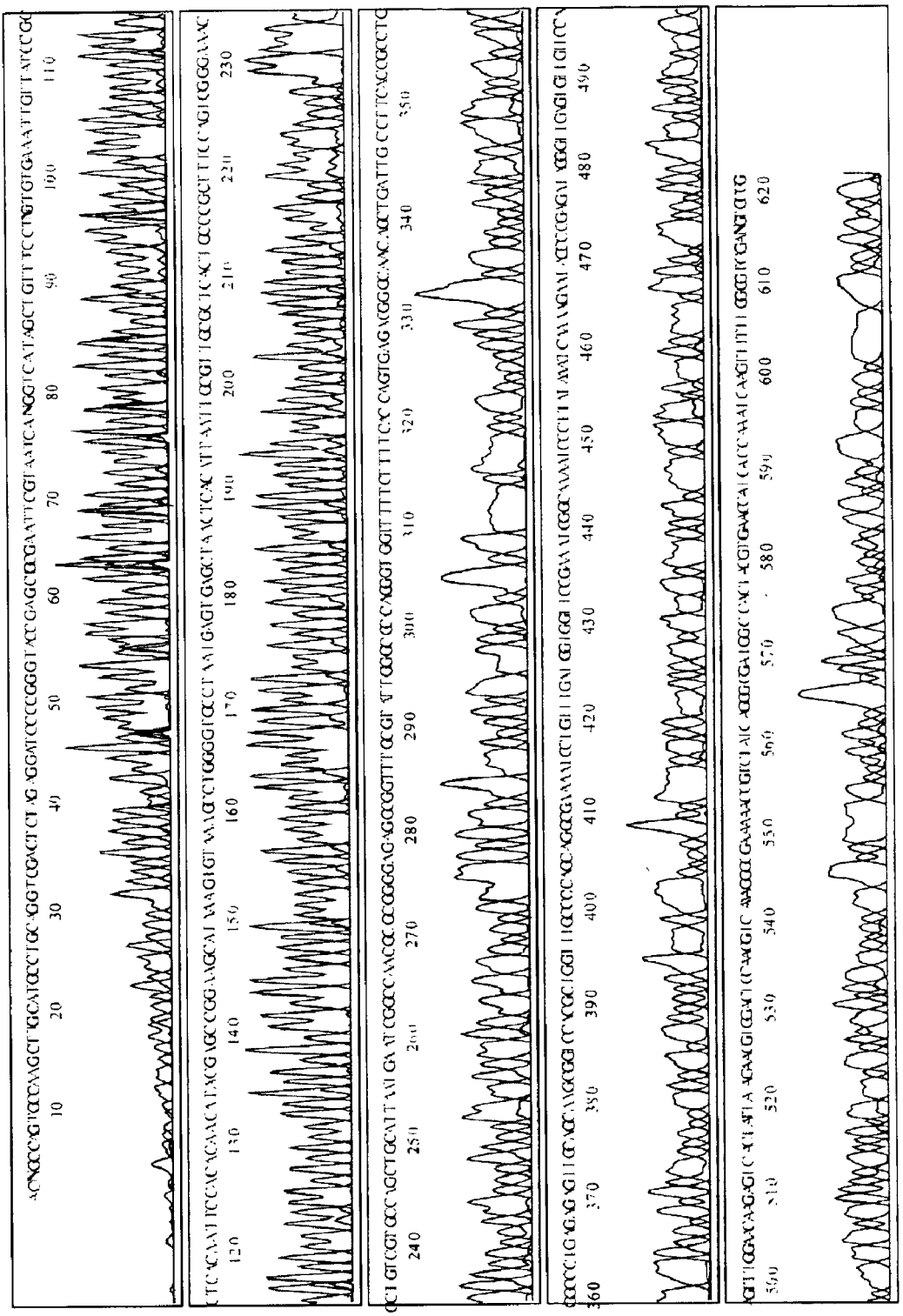
Figure 15:
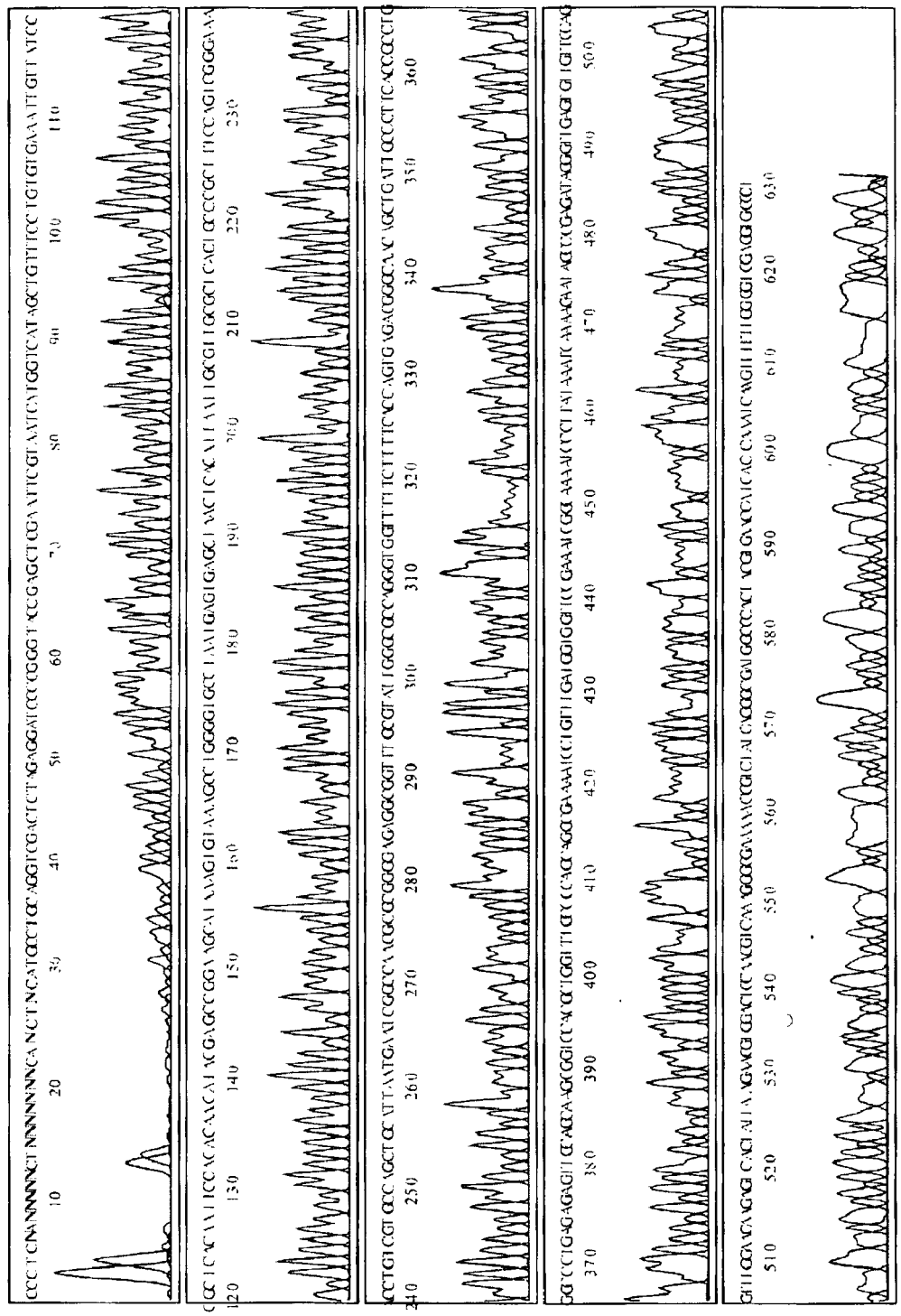
Figure 16:
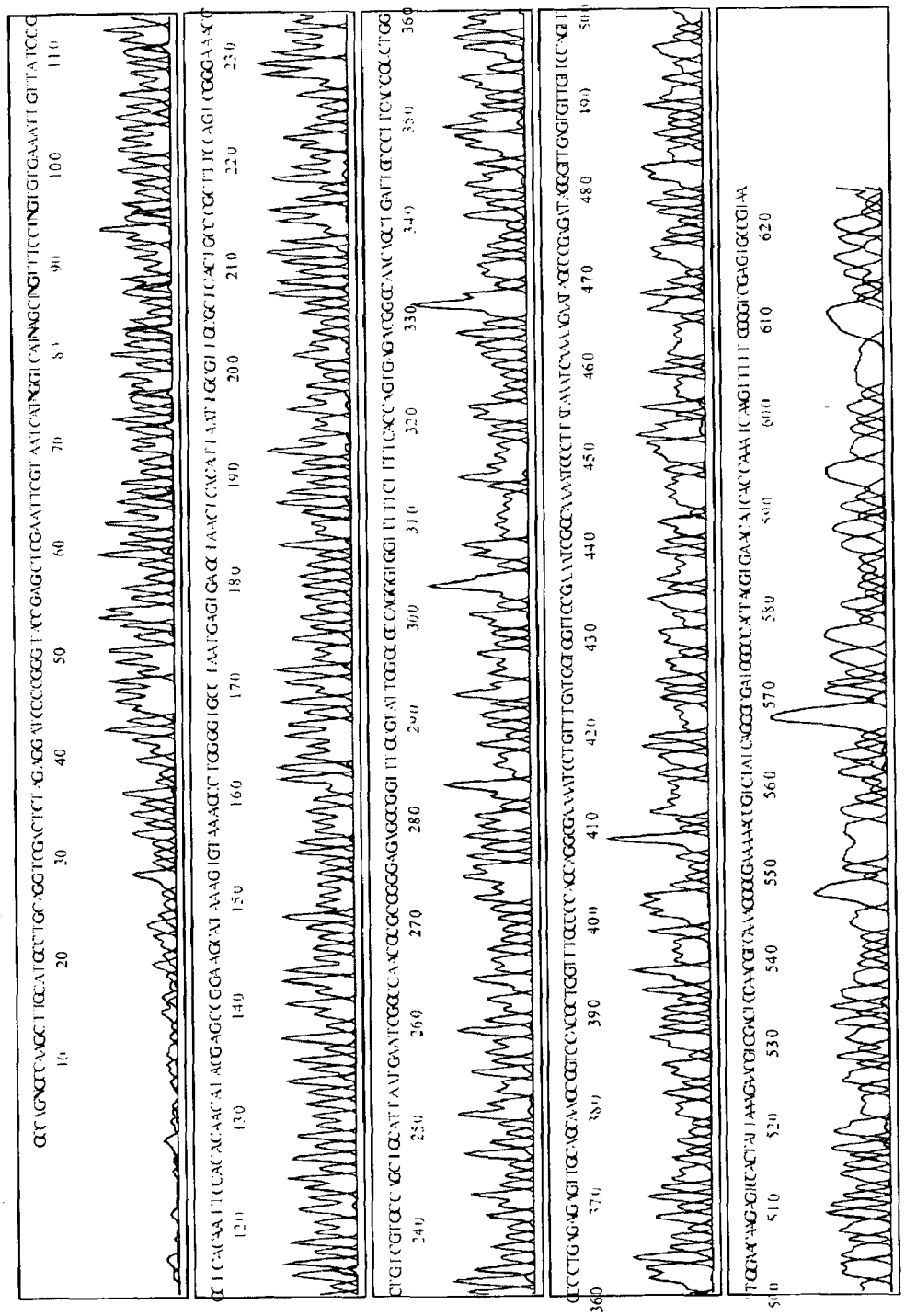

Thermostability at 95° C.:

The thermostability of Tsp JS1 Δ271//F667Y and Tsp JS1 Δ271//F667Y/E410R was assayed as follows. First, a 95° C. heating step was performed in a buffer containing 50 mM Tris-HCl pH 8.0, 1 mM $MgCl_2$, 35 mM KCl and 10% glycerol with polymerase at a concentration of 2 units/µl. At various times after the start of heating (0, 2, 5, 10 and 20 minutes), aliquots (20 µl each) were removed and immediately placed on ice. Next, dilutions were made and diluted samples were assayed for polymerase activity using a standard polymerase assay method (Davis, Fuller, Mamone & Huang WO 99/65938). FIG. 10 shows the results of the assays. The half-life of both Tsp JS1 Δ271//F667Y and Tsp JS1 Δ271//F667Y/E410R polymerases is apparently about 1 hour under these conditions at 95° C. Under the same conditions, the half-life of Taq polymerase, and that of FY7 (Davis, Fuller, Mamone & Huang WO 99/65938) was found to be less than 10 minutes.

2) Example 2

Uniform termination events for uniform band intensities:

The new polymerases also result in highly uniform termination events during sequencing reactions containing dye-labeled dideoxynucleotide terminators. This results uniform in electropherogram band intensities for determining long, accurate sequences. For example, as shown in FIGS. 11–16, the average variation of band intensity using the new polymerases averages less than about 25% deviation compared with the 20 closest bands.

It is apparent that many modifications and variations of the invention as hereinabove set forth may be made without departing from the spirit and scope thereof The specific embodiments described are given by way of example only, and the invention is limited only by the terms of the appended claims.

What is claimed is:

1. A purified recombinant thermostable DNA polymerase comprising the amino acid sequence set forth in FIG. 2.

2. A method for synthesizing a fluorescently labeled polynucleotide, comprising the step of mixing the DNA polymerase of claim 1 with a primed template.

3. The method of claim 2, wherein the primed template is a primed template in a chain termination sequencing reaction.

4. The method according to claim 2, wherein the primed template is a primed template in a polymerase chain reaction.

5. A kit for synthesizing fluorescently labeled polynucleotides comprising the polymerase of claim 1 and a fluorescently labeled nucleotide.

* * * * *

SEQUENCE LISTING

<160> NUMBER OF SEQ ID NOS: 18

<210> SEQ ID NO 1
<211> LENGTH: 834
<212> TYPE: PRT
<213> ORGANISM: Thermus thermophilus

<400> SEQUENCE: 1

-continued

```
Met Glu Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415
```

-continued

```
Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
        435                 440                 445

Thr Gly Val Arg Arg Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
    770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly
```

<210> SEQ ID NO 2
<211> LENGTH: 833
<212> TYPE: PRT
<213> ORGANISM: Thermus sp.

<400> SEQUENCE: 2

Met Arg Gly Met Leu Pro Leu Phe Glu Pro Lys Gly Arg Val Leu Leu
1               5                   10                  15

Val Asp Gly His His Leu Ala Tyr Arg Asn Phe Phe Ala Leu Lys Gly
            20                  25                  30

Leu Thr Thr Ser Arg Gly Glu Pro Val Gln Gly Val Tyr Gly Phe Ala
        35                  40                  45

Lys Ser Leu Leu Lys Ala Leu Lys Glu Asp Gly Asp Val Val Ile Val
    50                  55                  60

Val Phe Asp Ala Lys Ala Pro Ser Phe Arg His Glu Ala Tyr Glu Ala
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Glu Arg Leu Glu
            100                 105                 110

Val Pro Gly Phe Glu Ala Asp Asp Val Leu Ala Thr Leu Ala Lys Gln
        115                 120                 125

Ala Glu Arg Glu Gly Tyr Glu Val Arg Ile Leu Thr Ala Asp Arg Asp
    130                 135                 140

Leu Phe Gln Leu Leu Ser Asp Arg Ile Ala Val Leu His Pro Glu Gly
145                 150                 155                 160

His Leu Ile Thr Pro Gly Trp Leu Trp Glu Arg Tyr Gly Leu Lys Pro
                165                 170                 175

Glu Gln Trp Val Asp Phe Arg Ala Leu Ala Gly Asp Pro Ser Asp Asn
            180                 185                 190

Ile Pro Gly Val Lys Gly Ile Gly Glu Lys Thr Ala Leu Lys Leu Leu
        195                 200                 205

Lys Glu Trp Gly Ser Leu Glu Asn Leu Leu Lys Asn Leu Asp His Val
    210                 215                 220

Lys Pro Pro Ser Val Arg Glu Lys Ile Leu Ala His Leu Asp Asp Leu
225                 230                 235                 240

Arg Leu Ser Gln Glu Leu Ser Arg Val Arg Thr Asp Leu Pro Leu Lys
                245                 250                 255

Val Asp Phe Lys Lys Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Leu Pro Ala Glu Glu Ala Pro Trp Pro Pro Pro Glu
    290                 295                 300

Gly Ala Phe Leu Gly Tyr Arg Leu Ser Arg Pro Glu Pro Met Trp Ala
305                 310                 315                 320

Glu Leu Leu Ala Leu Ala Ala Ser Ala Lys Gly Arg Val Tyr Arg Ala
                325                 330                 335

Glu Glu Pro Tyr Gly Ala Leu Arg Gly Leu Lys Glu Val Arg Gly Leu
            340                 345                 350

Leu Ala Lys Asp Leu Ala Val Leu Ala Leu Arg Glu Gly Leu Asp Leu
        355                 360                 365

Pro Pro Thr Asp Asp Pro Met Leu Leu Ala Tyr Leu Leu Asp Pro Ser

-continued

```
            370                 375                 380
Asn Thr Thr Pro Glu Gly Val Ala Arg Arg Tyr Gly Gly Glu Trp Thr
385                 390                 395                 400
Glu Glu Ala Gly Glu Arg Ala Val Leu Ser Glu Arg Leu Tyr Glu Asn
                    405                 410                 415
Leu Leu Gly Arg Leu Arg Gly Glu Glu Lys Leu Leu Trp Leu Tyr Glu
                420                 425                 430
Glu Val Glu Lys Pro Leu Ser Arg Val Leu Ala His Met Glu Ala Thr
            435                 440                 445
Gly Val Arg Leu Asp Val Ala Tyr Leu Lys Ala Leu Ser Leu Glu Val
450                 455                 460
Ala Glu Glu Met Arg Arg Leu Glu Glu Glu Val Phe Arg Leu Ala Gly
465                 470                 475                 480
His Pro Phe Asn Leu Asn Ser Arg Asp Gln Leu Glu Arg Val Leu Phe
                485                 490                 495
Asp Glu Leu Gly Leu Pro Pro Ile Gly Lys Thr Glu Lys Thr Gly Lys
                500                 505                 510
Arg Ser Thr Ser Ala Ala Val Leu Glu Ala Leu Arg Glu Ala His Pro
            515                 520                 525
Ile Val Glu Lys Ile Leu Gln Tyr Arg Glu Leu Ala Lys Leu Lys Gly
            530                 535                 540
Thr Tyr Ile Asp Pro Leu Pro Ala Leu Val His Pro Lys Thr Gly Arg
545                 550                 555                 560
Leu His Thr Arg Phe Asn Gln Thr Ala Thr Ala Thr Gly Arg Leu Ser
                565                 570                 575
Ser Ser Asp Pro Asn Leu Gln Asn Ile Pro Val Arg Thr Pro Leu Gly
                580                 585                 590
Gln Arg Ile Arg Arg Ala Phe Val Ala Glu Glu Gly Tyr Leu Leu Val
            595                 600                 605
Ala Leu Asp Tyr Ser Gln Ile Glu Leu Arg Val Leu Ala His Leu Ser
            610                 615                 620
Gly Asp Glu Asn Leu Ile Gln Val Phe Gln Glu Gly Arg Asp Ile His
625                 630                 635                 640
Thr Gln Thr Ala Ser Trp Met Phe Gly Leu Pro Ala Glu Ala Ile Asp
                645                 650                 655
Pro Leu Met Arg Arg Ala Ala Lys Thr Ile Asn Phe Gly Val Leu Tyr
                660                 665                 670
Gly Met Ser Ala His Arg Leu Ser Gln Glu Leu Ser Ile Pro Tyr Glu
                675                 680                 685
Glu Ala Val Ala Phe Ile Asp Arg Tyr Phe Gln Ser Tyr Pro Lys Val
                690                 695                 700
Lys Ala Trp Ile Glu Arg Thr Leu Glu Glu Gly Arg Gln Arg Gly Tyr
705                 710                 715                 720
Val Glu Thr Leu Phe Gly Arg Arg Arg Tyr Val Pro Asp Leu Asn Ala
                    725                 730                 735
Arg Val Lys Ser Val Arg Glu Ala Ala Glu Arg Met Ala Phe Asn Met
                740                 745                 750
Pro Val Gln Gly Thr Ala Ala Asp Leu Met Lys Leu Ala Met Val Arg
                755                 760                 765
Leu Phe Pro Arg Leu Pro Glu Val Gly Ala Arg Met Leu Leu Gln Val
            770                 775                 780
His Asp Glu Leu Leu Leu Glu Ala Pro Lys Glu Arg Ala Glu Ala Ala
785                 790                 795                 800
```

Ala Ala Leu Ala Lys Glu Val Met Glu Gly Val Trp Pro Leu Ala Val
            805                 810                 815
Pro Leu Glu Val Glu Val Gly Ile Gly Glu Asp Trp Leu Ser Ala Lys
            820                 825                 830
Glu

<210> SEQ ID NO 3
<211> LENGTH: 832
<212> TYPE: PRT
<213> ORGANISM: Thermus aquaticus

<400> SEQUENCE: 3

Met Arg Gly Met Leu Pro Leu Phe Glu Pro Lys Gly Arg Val Leu Leu
 1               5                  10                  15
Val Asp Gly His His Leu Ala Tyr Arg Thr Phe His Ala Leu Lys Gly
            20                  25                  30
Leu Thr Thr Ser Arg Gly Glu Pro Val Gln Ala Val Tyr Gly Phe Ala
        35                  40                  45
Lys Ser Leu Leu Lys Ala Leu Lys Glu Asp Gly Asp Ala Val Ile Val
    50                  55                  60
Val Phe Asp Ala Lys Ala Pro Ser Phe Arg His Glu Ala Tyr Gly Gly
65                  70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Leu Gly Leu Ala Arg Leu Glu
            100                 105                 110
Val Pro Gly Tyr Glu Ala Asp Asp Val Leu Ala Ser Leu Ala Lys Lys
        115                 120                 125
Ala Glu Lys Glu Gly Tyr Glu Val Arg Ile Leu Thr Ala Asp Lys Asp
    130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
        195                 200                 205
Glu Glu Trp Gly Ser Leu Glu Ala Leu Leu Lys Asn Leu Asp Arg Leu
    210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
        275                 280                 285
Glu Ser Pro Lys Ala Leu Glu Glu Ala Pro Trp Pro Pro Pro Glu Gly
    290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335

-continued

```
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
            355                 360                 365
Pro Gly Asp Asp Pro Met Leu Leu Ala Tyr Leu Leu Asp Pro Ser Asn
            370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Arg Leu Leu Trp Leu Tyr Arg Glu
            420                 425                 430
Val Glu Arg Pro Leu Ser Ala Val Leu Ala His Met Glu Ala Thr Gly
            435                 440                 445
Val Arg Leu Asp Val Ala Tyr Leu Arg Ala Leu Ser Leu Glu Val Ala
    450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
            515                 520                 525
Val Glu Lys Ile Leu Gln Tyr Arg Glu Leu Thr Lys Leu Lys Ser Thr
            530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Gly Phe Ile Ala Glu Glu Gly Trp Leu Leu Val Ala
        595                 600                 605
Leu Asp Tyr Ser Gln Ile Glu Leu Arg Val Leu Ala His Leu Ser Gly
            610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
            690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
```

```
Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 4
<211> LENGTH: 561
<212> TYPE: PRT
<213> ORGANISM: Thermus sp.

<400> SEQUENCE: 4

Met Leu Glu Arg Leu Glu Phe Gly Ser Leu His Glu Phe Gly Leu
  1               5                  10                  15

Leu Glu Ser Pro Leu Pro Ala Glu Glu Ala Pro Trp Pro Pro Glu
                 20                  25                  30

Gly Ala Phe Leu Gly Tyr Arg Leu Ser Arg Pro Glu Pro Met Trp Ala
             35                  40                  45

Glu Leu Leu Ala Leu Ala Ala Ser Ala Lys Gly Arg Val Tyr Arg Ala
 50                  55                  60

Glu Glu Pro Tyr Gly Ala Leu Arg Gly Leu Lys Glu Val Arg Gly Leu
 65                  70                  75                  80

Leu Ala Lys Asp Leu Ala Val Leu Ala Leu Arg Glu Gly Leu Asp Leu
                 85                  90                  95

Pro Pro Thr Asp Asp Pro Met Leu Leu Ala Tyr Leu Leu Asp Pro Ser
            100                 105                 110

Asn Thr Thr Pro Glu Gly Val Ala Arg Arg Tyr Gly Gly Glu Trp Thr
            115                 120                 125

Glu Glu Ala Gly Glu Arg Ala Val Leu Ser Glu Arg Leu Tyr Glu Asn
130                 135                 140

Leu Leu Gly Arg Leu Arg Gly Glu Glu Lys Leu Leu Trp Leu Tyr Glu
145                 150                 155                 160

Glu Val Glu Lys Pro Leu Ser Arg Val Leu Ala His Met Glu Ala Thr
                165                 170                 175

Gly Val Arg Leu Asp Val Ala Tyr Leu Lys Ala Leu Ser Leu Glu Val
            180                 185                 190

Ala Glu Glu Met Arg Arg Leu Glu Glu Glu Val Phe Arg Leu Ala Gly
            195                 200                 205

His Pro Phe Asn Leu Asn Ser Arg Asp Gln Leu Glu Arg Val Leu Phe
210                 215                 220

Asp Glu Leu Gly Leu Pro Pro Ile Gly Lys Thr Glu Lys Thr Gly Lys
225                 230                 235                 240

Arg Ser Thr Ser Ala Ala Val Leu Glu Ala Leu Arg Glu Ala His Pro
                245                 250                 255

Ile Val Glu Lys Ile Leu Gln Tyr Arg Glu Leu Ala Lys Leu Lys Gly
            260                 265                 270

Thr Tyr Ile Asp Pro Leu Pro Ala Leu Val His Pro Lys Thr Gly Arg
            275                 280                 285

Leu His Thr Arg Phe Asn Gln Thr Ala Thr Ala Thr Gly Arg Leu Ser
290                 295                 300
```

```
Ser Ser Asp Pro Asn Leu Gln Asn Ile Pro Val Arg Thr Pro Leu Gly
305                 310                 315                 320

Gln Arg Ile Arg Arg Ala Phe Val Ala Glu Glu Gly Tyr Leu Leu Val
                325                 330                 335

Ala Leu Asp Tyr Ser Gln Ile Glu Leu Arg Val Leu Ala His Leu Ser
                340                 345                 350

Gly Asp Glu Asn Leu Ile Gln Val Phe Gln Gly Arg Asp Ile His
                355                 360                 365

Thr Gln Thr Ala Ser Trp Met Phe Gly Leu Pro Ala Glu Ala Ile Asp
370                 375                 380

Pro Leu Met Arg Arg Ala Ala Lys Thr Ile Asn Tyr Gly Val Leu Tyr
385                 390                 395                 400

Gly Met Ser Ala His Arg Leu Ser Gln Glu Leu Ser Ile Pro Tyr Glu
                405                 410                 415

Glu Ala Val Ala Phe Ile Asp Arg Tyr Phe Gln Ser Tyr Pro Lys Val
                420                 425                 430

Lys Ala Trp Ile Glu Arg Thr Leu Glu Glu Gly Arg Gln Arg Gly Tyr
                435                 440                 445

Val Glu Thr Leu Phe Gly Arg Arg Arg Tyr Val Pro Asp Leu Asn Ala
450                 455                 460

Arg Val Lys Ser Val Arg Glu Ala Ala Glu Arg Met Ala Phe Asn Met
465                 470                 475                 480

Pro Val Gln Gly Thr Ala Ala Asp Leu Met Lys Leu Ala Met Val Arg
                485                 490                 495

Leu Phe Pro Arg Leu Pro Glu Val Gly Ala Arg Met Leu Leu Gln Val
                500                 505                 510

His Asp Glu Leu Leu Glu Ala Pro Lys Glu Arg Ala Glu Ala Ala
                515                 520                 525

Ala Ala Leu Ala Lys Glu Val Met Glu Gly Val Trp Pro Leu Ala Val
                530                 535                 540

Pro Leu Glu Val Glu Val Gly Ile Gly Glu Asp Trp Leu Ser Ala Lys
545                 550                 555                 560

Glu

<210> SEQ ID NO 5
<211> LENGTH: 561
<212> TYPE: PRT
<213> ORGANISM: Thermus sp.

<400> SEQUENCE: 5

Met Leu Glu Arg Leu Glu Phe Gly Ser Leu Leu His Glu Phe Gly Leu
  1               5                  10                  15

Leu Glu Ser Pro Leu Pro Ala Glu Glu Ala Pro Trp Pro Pro Pro Glu
                 20                  25                  30

Gly Ala Phe Leu Gly Tyr Arg Leu Ser Arg Pro Glu Pro Met Trp Ala
                35                  40                  45

Glu Leu Leu Ala Leu Ala Ala Ser Ala Lys Gly Arg Val Tyr Arg Ala
         50                  55                  60

Glu Glu Pro Tyr Gly Ala Leu Arg Gly Leu Lys Glu Val Arg Gly Leu
 65                  70                  75                  80

Leu Ala Lys Asp Leu Ala Val Leu Ala Leu Arg Glu Gly Leu Asp Leu
                 85                  90                  95

Pro Pro Thr Asp Asp Pro Met Leu Leu Ala Tyr Leu Leu Asp Pro Ser
                100                 105                 110
```

-continued

```
Asn Thr Thr Pro Glu Val Ala Arg Arg Tyr Gly Gly Glu Trp Thr
            115                 120                 125
Glu Glu Ala Gly Glu Arg Ala Val Leu Ser Glu Arg Leu Tyr Glu Asn
130                 135                 140
Leu Leu Gly Arg Leu Arg Gly Glu Glu Lys Leu Leu Trp Leu Tyr Glu
145                 150                 155                 160
Glu Val Glu Lys Pro Leu Ser Arg Val Leu Ala His Met Glu Ala Thr
                165                 170                 175
Gly Val Arg Leu Asp Val Ala Tyr Leu Lys Ala Leu Ser Leu Glu Val
            180                 185                 190
Ala Glu Glu Met Arg Arg Leu Glu Glu Val Phe Arg Leu Ala Gly
            195                 200                 205
His Pro Phe Asn Leu Asn Ser Arg Asp Gln Leu Glu Arg Val Leu Phe
            210                 215                 220
Asp Glu Leu Gly Leu Pro Pro Ile Gly Lys Thr Glu Lys Thr Gly Lys
225                 230                 235                 240
Arg Ser Thr Ser Ala Ala Val Leu Glu Ala Leu Arg Glu Ala His Pro
                245                 250                 255
Ile Val Glu Lys Ile Leu Gln Tyr Arg Glu Leu Ala Lys Leu Lys Gly
                260                 265                 270
Thr Tyr Ile Asp Pro Leu Pro Ala Leu Val His Pro Lys Thr Gly Arg
            275                 280                 285
Leu His Thr Arg Phe Asn Gln Thr Ala Thr Ala Thr Gly Arg Leu Ser
            290                 295                 300
Ser Ser Asp Pro Asn Leu Gln Asn Ile Pro Val Arg Thr Pro Leu Gly
305                 310                 315                 320
Gln Arg Ile Arg Arg Ala Phe Val Ala Glu Glu Gly Tyr Leu Leu Val
                325                 330                 335
Ala Leu Asp Tyr Ser Gln Ile Glu Leu Arg Val Leu Ala His Leu Ser
            340                 345                 350
Gly Asp Glu Asn Leu Ile Gln Val Phe Gln Glu Gly Arg Asp Ile His
            355                 360                 365
Thr Gln Thr Ala Ser Trp Met Phe Gly Leu Pro Ala Glu Ala Ile Asp
370                 375                 380
Pro Leu Met Arg Arg Ala Ala Lys Thr Ile Asn Tyr Gly Val Leu Tyr
385                 390                 395                 400
Gly Met Ser Ala His Arg Leu Ser Gln Arg Leu Ser Ile Pro Tyr Glu
                405                 410                 415
Glu Ala Val Ala Phe Ile Asp Arg Tyr Phe Gln Ser Tyr Pro Lys Val
                420                 425                 430
Lys Ala Trp Ile Glu Arg Thr Leu Glu Glu Gly Arg Gln Arg Gly Tyr
            435                 440                 445
Val Glu Thr Leu Phe Gly Arg Arg Arg Tyr Val Pro Asp Leu Asn Ala
            450                 455                 460
Arg Val Lys Ser Val Arg Glu Ala Ala Glu Arg Met Ala Phe Asn Met
465                 470                 475                 480
Pro Val Gln Gly Thr Ala Ala Asp Leu Met Lys Leu Ala Met Val Arg
                485                 490                 495
Leu Phe Pro Arg Leu Pro Glu Val Gly Ala Arg Met Leu Leu Gln Val
            500                 505                 510
His Asp Glu Leu Leu Leu Glu Ala Pro Lys Glu Arg Ala Glu Ala Ala
            515                 520                 525
```

```
Ala Ala Leu Ala Lys Glu Val Met Glu Gly Val Trp Pro Leu Ala Val
        530                 535                 540
Pro Leu Glu Val Glu Val Gly Ile Gly Glu Asp Trp Leu Ser Ala Lys
545                 550                 555                 560
Glu

<210> SEQ ID NO 6
<211> LENGTH: 834
<212> TYPE: PRT
<213> ORGANISM: Thermus thermophilus

<400> SEQUENCE: 6

Met Glu Ala Met Leu Pro Leu Phe Glu Pro Lys Gly Arg Val Leu Leu
  1               5                  10                  15
Val Ala Gly His His Leu Ala Tyr Arg Thr Phe Phe Ala Leu Lys Gly
                 20                  25                  30
Leu Thr Thr Ser Arg Gly Glu Pro Val Gln Ala Val Tyr Gly Phe Ala
             35                  40                  45
Lys Ser Leu Leu Lys Ala Leu Lys Glu Asp Gly Tyr Lys Ala Val Phe
         50                  55                  60
Val Val Phe Asp Ala Lys Ala Pro Ser Phe Arg His Glu Ala Tyr Glu
 65                  70                  75                  80
Ala Tyr Lys Ala Gly Arg Ala Pro Thr Pro Glu Asp Phe Pro Arg Gln
                 85                  90                  95
Leu Ala Leu Ile Lys Glu Leu Val Asp Leu Leu Gly Phe Thr Arg Leu
            100                 105                 110
Glu Val Pro Gly Tyr Glu Ala Asp Asp Val Leu Ala Thr Leu Ala Lys
        115                 120                 125
Lys Ala Glu Lys Glu Gly Tyr Glu Val Arg Ile Leu Thr Ala Asp Arg
    130                 135                 140
Asp Leu Tyr Gln Leu Val Ser Asp Arg Val Ala Val Leu His Pro Glu
145                 150                 155                 160
Gly His Leu Ile Thr Pro Glu Trp Leu Trp Glu Lys Tyr Gly Leu Arg
                165                 170                 175
Pro Glu Gln Trp Val Asp Phe Arg Ala Leu Val Gly Asp Pro Ser Asp
            180                 185                 190
Asn Leu Pro Gly Val Lys Gly Ile Gly Glu Lys Thr Ala Leu Lys Leu
        195                 200                 205
Leu Lys Glu Trp Gly Ser Leu Glu Asn Leu Leu Lys Asn Leu Asp Arg
    210                 215                 220
Val Lys Pro Glu Asn Val Arg Glu Lys Ile Lys Ala His Leu Glu Asp
225                 230                 235                 240
Leu Arg Leu Ser Leu Glu Leu Ser Arg Val Arg Thr Asp Leu Pro Leu
                245                 250                 255
Glu Val Asp Leu Ala Gln Gly Arg Glu Pro Asp Arg Glu Gly Leu Arg
            260                 265                 270
Ala Phe Leu Glu Arg Leu Glu Phe Gly Ser Leu Leu His Glu Phe Gly
        275                 280                 285
Leu Leu Glu Ala Pro Ala Pro Leu Glu Glu Ala Pro Trp Pro Pro Pro
    290                 295                 300
Glu Gly Ala Phe Val Gly Phe Val Leu Ser Arg Pro Glu Pro Met Trp
305                 310                 315                 320
Ala Glu Leu Lys Ala Leu Ala Ala Cys Arg Asp Gly Arg Val His Arg
                325                 330                 335
```

```
Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
            355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Arg Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Tyr Gly Val Leu
            660                 665                 670

Tyr Gly Met Ser Ala His Arg Leu Ser Gln Arg Leu Ala Ile Pro Tyr
            675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
```

-continued

```
                755                 760                 765
Lys Leu Phe Pro Arg Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
                820                 825                 830

Lys Gly

<210> SEQ ID NO 7
<211> LENGTH: 561
<212> TYPE: PRT
<213> ORGANISM: Thermus thermophilus

<400> SEQUENCE: 7

Met Leu Glu Arg Leu Glu Phe Gly Ser Leu Leu His Glu Phe Gly Leu
  1               5                  10                  15

Leu Glu Ala Pro Ala Pro Leu Glu Glu Ala Pro Trp Pro Pro Pro Glu
                 20                  25                  30

Gly Ala Phe Val Gly Phe Val Leu Ser Arg Pro Glu Pro Met Trp Ala
             35                  40                  45

Glu Leu Lys Ala Leu Ala Ala Cys Arg Asp Gly Arg Val His Arg Ala
         50                  55                  60

Ala Asp Pro Leu Ala Gly Leu Lys Asp Leu Lys Glu Val Arg Gly Leu
 65                  70                  75                  80

Leu Ala Lys Asp Leu Ala Val Leu Ala Ser Arg Glu Gly Leu Asp Leu
                 85                  90                  95

Val Pro Gly Asp Asp Pro Met Leu Leu Ala Tyr Leu Leu Asp Pro Ser
                100                 105                 110

Asn Thr Thr Pro Glu Gly Val Ala Arg Arg Tyr Gly Gly Glu Trp Thr
            115                 120                 125

Glu Asp Ala Ala His Arg Ala Leu Leu Ser Glu Arg Leu His Arg Asn
        130                 135                 140

Leu Leu Lys Arg Leu Glu Gly Glu Glu Lys Leu Leu Trp Leu Tyr His
145                 150                 155                 160

Glu Val Glu Lys Pro Leu Ser Arg Val Leu Ala His Met Glu Ala Thr
                165                 170                 175

Gly Val Arg Arg Asp Val Ala Tyr Leu Gln Ala Leu Ser Leu Glu Leu
                180                 185                 190

Ala Glu Glu Ile Arg Arg Leu Glu Glu Val Phe Arg Leu Ala Gly
            195                 200                 205

His Pro Phe Asn Leu Asn Ser Arg Asp Gln Leu Glu Arg Val Leu Phe
        210                 215                 220

Asp Glu Leu Arg Leu Pro Ala Leu Gly Lys Thr Gln Lys Thr Gly Lys
225                 230                 235                 240

Arg Ser Thr Ser Ala Ala Val Leu Glu Ala Leu Arg Glu Ala His Pro
                245                 250                 255

Ile Val Glu Lys Ile Leu Gln His Arg Glu Leu Thr Lys Leu Lys Asn
                260                 265                 270

Thr Tyr Val Asp Pro Leu Pro Ser Leu Val His Pro Arg Thr Gly Arg
            275                 280                 285

Leu His Thr Arg Phe Asn Gln Thr Ala Thr Ala Thr Gly Arg Leu Ser
```

```
                    290                 295                 300
Ser Ser Asp Pro Asn Leu Gln Asn Ile Pro Val Arg Thr Pro Leu Gly
305                 310                 315                 320

Gln Arg Ile Arg Arg Ala Phe Val Ala Glu Ala Gly Trp Ala Leu Val
                325                 330                 335

Ala Leu Asp Tyr Ser Gln Ile Glu Leu Arg Val Leu Ala His Leu Ser
            340                 345                 350

Gly Asp Glu Asn Leu Ile Arg Val Phe Gln Glu Gly Lys Asp Ile His
        355                 360                 365

Thr Gln Thr Ala Ser Trp Met Phe Gly Val Pro Pro Glu Ala Val Asp
370                 375                 380

Pro Leu Met Arg Arg Ala Ala Lys Thr Val Asn Tyr Gly Val Leu Tyr
385                 390                 395                 400

Gly Met Ser Ala His Arg Leu Ser Gln Arg Leu Ala Ile Pro Tyr Glu
                405                 410                 415

Glu Ala Val Ala Phe Ile Glu Arg Tyr Phe Gln Ser Phe Pro Lys Val
            420                 425                 430

Arg Ala Trp Ile Glu Lys Thr Leu Glu Glu Gly Arg Lys Arg Gly Tyr
        435                 440                 445

Val Glu Thr Leu Phe Gly Arg Arg Arg Tyr Val Pro Asp Leu Asn Ala
450                 455                 460

Arg Val Lys Ser Val Arg Glu Ala Ala Glu Arg Met Ala Phe Asn Met
465                 470                 475                 480

Pro Val Gln Gly Thr Ala Ala Asp Leu Met Lys Leu Ala Met Val Lys
                485                 490                 495

Leu Phe Pro Arg Leu Arg Glu Met Gly Ala Arg Met Leu Leu Gln Val
            500                 505                 510

His Asp Glu Leu Leu Leu Glu Ala Pro Gln Ala Arg Ala Glu Glu Val
        515                 520                 525

Ala Ala Leu Ala Lys Glu Ala Met Glu Lys Ala Tyr Pro Leu Ala Val
530                 535                 540

Pro Leu Glu Val Glu Val Gly Met Gly Glu Asp Trp Leu Ser Ala Lys
545                 550                 555                 560

Gly

<210> SEQ ID NO 8
<211> LENGTH: 2502
<212> TYPE: DNA
<213> ORGANISM: Thermus sp.

<400> SEQUENCE: 8
atgagaggca tgcttccact ttttgagccc aagggccggg tcctcctggt ggacggccac     60
cacctggcct accgcaactt tttcgccctc aaagggctca ccacgagccg ggcgagccg    120 gtgcaagggg tctacggctt cgccaaaagc ctcctcaagg ccctgaagga ggacggggac    180
gtggtcatcg tggtctttga cgccaaggcc ccctcttttcc gccacgaggc ctacgaggcc    240
tacaaggcgg gccggcccc cacccccgag gactttcccc ggcagctcgc cctcataaag    300
gagctggtgg acctcttggg gctggagcgc ctcgaggtcc gggctttga agcggacgat    360 gtcctcgcca ccttggccaa gcaagcggag cgggaagggt acgaggtgcg catcctcacc    420
gccgaccggg acctcttcca gctcctttcg gaccgcatcg ccgtcctcca cccggaaggg    480
cacctcatca cccggggtgt gctttgggag cggtacggtc tgaagccgga gcagtgggtg    540
gacttccgcg ccctggccgg cgacccctcc gacaacatcc ccggggtgaa gggaatcggg    600
```

-continued

```
gagaagaccg ccctgaagct cctcaaggag tggggagcc tggaaaacct cctcaagaac      660
ctggaccatg tgaagcctcc ttccgtaagg gagaagatcc tcgcccacct ggacgacctc      720
aggctctccc aggagctttc ccgggtgcgc acggacctcc ccttgaaggt ggactttaaa      780
aagcggcggg agcccgatag ggaagggctt aaggccttct ggagcggct tgagtttgga       840
agcctcctcc acgagttcgg cctcctggaa agccccttc cggcggagga ggccccatgg       900
ccgccgccgg aaggggcctt tttgggctac cgcctttccc ggcccgagcc catgtgggcg      960
gagcttcttg ccttggcggc gagcgccaag ggccgggttt accgggcgga ggagccctat     1020
ggggccctaa ggggcctgaa ggaggtgcgg gggcttcttg ccaaggacct cgccgtcttg     1080
gccctaaggg agggcctgga ccttcccccc acggacgacc ccatgctcct cgcttacctc     1140
ctggacccct ccaacaccac ccccgagggc gtggcccggc ggtatggggg ggagtggacg     1200
gaggaggcgg gggagcgggc ggtgctttcc gaaaggctct acgagaacct ccttgggcgc     1260
ttgagagggg aagagaagct cctttggctt tacgaggagg tggaaaagcc cctctcccgg     1320
gtcctcgccc acatggaggc cacggggtg aggctggacg tggcctacct caaggccctt     1380
tccctggagg tggcggagga gatgcgccgc ctggaggagg aggtcttccg cctggcgggc     1440
caccccttca acctcaattc ccgcgaccag ctggaaaggg tgctctttga cgagctcggc     1500
cttcccccca tcggcaagac ggagaagact gggaagcgct ccacgagcgc cgccgtcctc     1560
gaggccctgc gggaggccca ccccatcgtg gaaaagatcc ttcagtaccg gaactggcc     1620
aagctcaagg gcacctacat tgacccccct tcccgccctgg tccaccccaa gacggggcgg     1680
ctccacaccc gcttcaacca gacggccacg gccacgggcc gccttccag ctccgacccc     1740
aacctgcaga acatccccgt gcgcaccccc ttgggccaaa ggatccgccg ggccttcgtg     1800
gccgaggagg ggtacctgct cgtggccctg gactatagcc agattgagct cagggtcctg     1860
gcccacctct cggggacga gaacctcatc caggtcttcc aggagggccg ggacatccac     1920
acccagacgg cgagctggat gttcggcctg ccggcggagg ccatagaccc cctcatgcgc     1980
cgggcggcca agaccatcaa cttcggcgtc ctttacggca tgtccgccca tcggctttcc     2040
caagagctca gcatcccta cgaggaggcg gtggccttca ttgaccgcta tttccagagc     2100
taccccaagg tgaaggcctg gattgaaagg accctggagg agggggcggca gaggggtat      2160
gtggaaaccc tcttcggccg caggcgctac gtgcccgacc tcaacgcccg ggtaaagagc     2220
gtgcgggagg cggcggagcg catggccttt aacatgcccg tgcagggcac cgccgccgac     2280
ctgatgaagc tcgccatggt gaggcttttc cccaggcttc ccgaggtggg ggcgcggatg     2340
ctcctccagg tgcacgacga gctcctcctg gaggcgccca aggagcgggc ggaggcggcg     2400
gcggccctgg ccaaggaggt catggagggg gtctggcccc tggccgtgcc cctggaggtg     2460
gaggtgggga taggggagga ctggctctcc gccaaggagt ga                        2502
```

<210> SEQ ID NO 9
<211> LENGTH: 626
<212> TYPE: DNA
<213> ORGANISM: Thermus sp.
<220> FEATURE:
<221> NAME/KEY: modified_base
<222> LOCATION: (5)
<223> OTHER INFORMATION: a, t, c, g, other or unknown
<220> FEATURE:
<221> NAME/KEY: modified_base
<222> LOCATION: (16)
<223> OTHER INFORMATION: a, t, c, g, other or unknown
<220> FEATURE:

<220> FEATURE:
<221> NAME/KEY: modified_base
<222> LOCATION: (479)
<223> OTHER INFORMATION: a, t, c, g, other or unknown
<220> FEATURE:
<221> NAME/KEY: modified_base
<222> LOCATION: (517)
<223> OTHER INFORMATION: a, t, c, g, other or unknown
<220> FEATURE:
<221> NAME/KEY: modified_base
<222> LOCATION: (586)
<223> OTHER INFORMATION: a, t, c, g, other or unknown
<220> FEATURE:
<221> NAME/KEY: modified_base
<222> LOCATION: (595)
<223> OTHER INFORMATION: a, t, c, g, other or unknown
<220> FEATURE:
<221> NAME/KEY: modified_base
<222> LOCATION: (616)
<223> OTHER INFORMATION: a, t, c, g, other or unknown

<400> SEQUENCE: 9

| | | | | | |
|---|---|---|---|---|---|
| ctggnaaacg | acggcnagtg | ccaagcttgc | atgcctgcag | gtcgactcta | gaggatcccc | 60 |
| gggtaccgag | ctcgaattcg | taatcatggt | catagctgtt | tcctgtgtga | aattgttatc | 120 |
| cggctcacaa | ttccacacaa | catacgagcc | ggaagcataa | agtgtaaagc | ctggggtgcc | 180 |
| taatgagtga | gctaactcac | attaattgcg | ttgcgctcac | tgcccgcttt | ccagtcggga | 240 |
| aaacctgtcg | tgccagctgc | attaatgaat | cggccaacgc | gcggggagag | gcggtttgcg | 300 |
| tattgggcgc | cagggtggtt | tttcttttca | ccagtgagac | gggcaacagc | tgattggcct | 360 |
| tcaccgccct | ggccctgaga | gagttgcagc | aagcggtcca | cgctggtttg | ccccagcagg | 420 |
| cgaaaatcct | gtttgatggt | ggttccgaaa | tcggcaaaat | ccttataatc | aaagaatanc | 480 |
| cgagataggg | ttgagtgttg | gtccagttgg | acaagantca | tattaagaac | gtgactcaac | 540 |
| tcaaaggcga | aaacctctat | caggcgatgg | ccactactga | acctcnccaa | tcaanttttt | 600 |
| ggggtcaagg | tgcctnaaca | ctaaat | | | | 626 |

<210> SEQ ID NO 10
<211> LENGTH: 632
<212> TYPE: DNA
<213> ORGANISM: Thermus sp.
<220> FEATURE:
<221> NAME/KEY: modified_base
<222> LOCATION: (3)
<223> OTHER INFORMATION: a, t, c, g, other or unknown
<220> FEATURE:
<221> NAME/KEY: modified_base
<222> LOCATION: (83)
<223> OTHER INFORMATION: a, t, c, g, other or unknown

<400> SEQUENCE: 10

| | | | | | |
|---|---|---|---|---|---|
| acngccagtg | ccaagcttgc | atgcctgcag | gtcgactcta | gaggatcccc | gggtaccgag | 60 |
| ctcgaattcg | taatcatggt | canagctgtt | tcctgtgtga | aattgttatc | cgcttcacaa | 120 |
| ttccacacaa | catacgagcc | ggaagcataa | agtgtaaagc | ctggggtgcc | taatgagtga | 180 |
| gctaactcac | attaattgcg | ttgcgctcac | tgcccgcttt | ccagtcggga | aaccttgtcg | 240 |
| tgccagctgc | attaatgaat | cggccaacgc | gcggggagag | gcggtttgcg | tattgggcgc | 300 |
| cagggtggtt | tttcttttca | ccagtgagac | gggcaacagc | tgattgccct | tcaccgcctg | 360 |
| gcccctgaga | gagttgcagc | aagcggtcca | cgctggtttg | cccagcaggc | gaaaatcctg | 420 |
| tttgatggtg | gttccgaaat | cggcaaaatc | cttataaat | caaagaata | gcccgagata | 480 |
| gggttgagtg | ttgttccagt | tttgaacaa | gagtccacta | ttaagaacgt | ggactccaac | 540 |
| gtcaaagggc | gaaaaaccgt | ctatcagggc | gatggccact | acgtgaacca | tcaccaaatc | 600 |

```
aagtttttttg gggtcaagtg ccgtaagcac ta                                        632
```

<210> SEQ ID NO 11
<211> LENGTH: 631
<212> TYPE: DNA
<213> ORGANISM: Thermus sp.
<220> FEATURE:
<221> NAME/KEY: modified_base
<222> LOCATION: (1)..(2)
<223> OTHER INFORMATION: a, t, c, g, other or unknown
<220> FEATURE:
<221> NAME/KEY: modified_base
<222> LOCATION: (4)..(11)
<223> OTHER INFORMATION: a, t, c, g, other or unknown
<220> FEATURE:
<221> NAME/KEY: modified_base
<222> LOCATION: (13)..(14)
<223> OTHER INFORMATION: a, t, c, g, other or unknown
<220> FEATURE:
<221> NAME/KEY: modified_base
<222> LOCATION: (16)
<223> OTHER INFORMATION: a, t, c, g, other or unknown
<220> FEATURE:
<221> NAME/KEY: modified_base
<222> LOCATION: (551)
<223> OTHER INFORMATION: a, t, c, g, other or unknown
<220> FEATURE:
<221> NAME/KEY: modified_base
<222> LOCATION: (579)
<223> OTHER INFORMATION: a, t, c, g, other or unknown

<400> SEQUENCE: 11

```
nntnnnnnnn nanngncagt gccaagcttg catgcctgca ggtcgactct agaggatccc    60
cgggtaccga gctcgaattc gtaatcatgg tcatagctgt ttcctgtgtg aaattgttat   120
ccggctcaca attccacaca acatacgagc cggaagcata aagtgtaaag cctggggtgc   180
ctaatgagtg agctaactca cattaattgc gttgcgctca ctgcccgctt tccagtcggg   240
aaacccgtgt cgtgccagct gcattaatga atcggccaac gcgcgggaga ggcggtttgc   300
gtattgggcg ccagggtggt ttttctttc accagtgaga cgggcaacag ctgattgccc   360
ttcaccgcct gggccctgag agagttgcag caagcggtcc acgctggttt gcccagcagg   420
cgaaaatcct gtttgatggt ggttccgaaa tcggcaaaat cccttataat caaagatagc   480
ccgagatagg gttgagtgtt gttccagttt tggaacaaga gtcactatta agaacgtgac   540
tcaacgtcaa nggcgaaaac cgtctatcag ggcgatggnc cactacgtga accatcacca   600
aatcaagttt tttgggggtcg aggtgccgta a                                 631
```

<210> SEQ ID NO 12
<211> LENGTH: 625
<212> TYPE: DNA
<213> ORGANISM: Thermus sp.
<220> FEATURE:
<221> NAME/KEY: modified_base
<222> LOCATION: (3)
<223> OTHER INFORMATION: a, t, c, g, other or unknown
<220> FEATURE:
<221> NAME/KEY: modified_base
<222> LOCATION: (78)
<223> OTHER INFORMATION: a, t, c, g, other or unknown
<220> FEATURE:
<221> NAME/KEY: modified_base
<222> LOCATION: (96)
<223> OTHER INFORMATION: a, t, c, g, other or unknown
<220> FEATURE:
<221> NAME/KEY: modified_base
<222> LOCATION: (619)
<223> OTHER INFORMATION: a, t, c, g, other or unknown -continued

```
<400> SEQUENCE: 12
acngccagtg ccaagcttgc atgcctgcag gtcgactcta gaggatcccc gggtaccgag      60
ctgcgaattc gtaatcangg tcatagctgt ttcctngtgt gaaattgtta tccgcctcac     120
aattccacac aacatacgag ccggaagcat aaagtgtaaa gcctggggtg cctaatgagt    180
gagctaactc acattaattg cgttgcgctc actgcccgct ttccagtcgg gaaaccctgt    240
cgtgccagct gcattaatga atcggccaac gcgcggggag aggcggtttg cgtattgggc   300
gccagggtgg ttttcttttt caccagtgag acgggcaaca gctgattgcc ttcaccgcct   360
gggccctgag agagttgcag caagcggtcc acgctggttt gccccagcag gcgaaaatcc    420
tgtttgatgg tggttccgaa atcggcaaaa tcccttataa atcaaaagaa tagcccgaga    480
tagggttgag tgttgttcca gtttggaac aagagtcact attaagaacg tggactccaa     540
cgtcaaaggg cgaaaaaccg tctatcaggg cgatggccac tacgtgaacc atcaccaaat   600 caagttttttt ggggtcgang tgccg                                          625

<210> SEQ ID NO 13
<211> LENGTH: 634
<212> TYPE: DNA
<213> ORGANISM: Thermus sp.
<220> FEATURE:
<221> NAME/KEY: modified_base
<222> LOCATION: (6)
<223> OTHER INFORMATION: a, t, c, g, other or unknown
<220> FEATURE:
<221> NAME/KEY: modified_base
<222> LOCATION: (8)..(12)
<223> OTHER INFORMATION: a, t, c, g, other or unknown
<220> FEATURE:
<221> NAME/KEY: modified_base
<222> LOCATION: (15)..(21)
<223> OTHER INFORMATION: a, t, c, g, other or unknown
<220> FEATURE:
<221> NAME/KEY: modified_base
<222> LOCATION: (24)
<223> OTHER INFORMATION: a, t, c, g, other or unknown
<220> FEATURE:
<221> NAME/KEY: modified_base
<222> LOCATION: (27)
<223> OTHER INFORMATION: a, t, c, g, other or unknown

<400> SEQUENCE: 13
ccctcnannn nnctnnnnnn ncanctncat gcctgcaggt cgactctaga ggatccccgg      60
gtaccgagct cgaattcgta atcatggtca tagctgtttc ctgtgtgaaa ttgttatccc    120
gctcacaatt ccacacaaca tacgagccgg aagcataaag tgtaaagcct ggggtgccta   180
atgagtgagc taactcacat taattgcgtt gcgctcactg cccgctttcc agtcgggaaa    240
acctgtcgtg ccagctgcat taatgaatcg gccaacgcgc ggggagaggc ggtttgcgta   300
ttgggcgcca gggtggtttt cttttcacc agtgagacgg gcaacagctg attgcccttc    360
accgcctggg ccctgagaga gttgcagcaa gcggtccacg ctggtttgcc ccagcaggcg   420
aaaatcctgt ttgatggtgg ttccgaaatc ggcaaaatcc cttataaatc aaaagaatag   480
cccgagatag ggttgagtgt tgttccaggt ttggaacaag agtcactatt aagaacgtgg   540
actccaacgt caaagggcga aaaccgtct atcagggcga tgcccacta cgtgaaccat    600 caccaaatca gttttttgg ggtcgaggtg ccct                                  634

<210> SEQ ID NO 14
<211> LENGTH: 628
<212> TYPE: DNA
<213> ORGANISM: Thermus sp.
```

```
<220> FEATURE:
<221> NAME/KEY: modified_base
<222> LOCATION: (6)
<223> OTHER INFORMATION: a, t, c, g, other or unknown
<220> FEATURE:
<221> NAME/KEY: modified_base
<222> LOCATION: (75)
<223> OTHER INFORMATION: a, t, c, g, other or unknown
<220> FEATURE:
<221> NAME/KEY: modified_base
<222> LOCATION: (82)
<223> OTHER INFORMATION: a, t, c, g, other or unknown
<220> FEATURE:
<221> NAME/KEY: modified_base
<222> LOCATION: (87)
<223> OTHER INFORMATION: a, t, c, g, other or unknown
<220> FEATURE:
<221> NAME/KEY: modified_base
<222> LOCATION: (95)
<223> OTHER INFORMATION: a, t, c, g, other or unknown

<400> SEQUENCE: 14
gccagngcca agcttgcatg cctgcaggtc gactctagag gatccccggg taccgagctc      60
gaattcgtaa tcatnggtca tnagctngtt cctngtgtg aaattgttat ccggctcaca     120
attccacaca acatacgagc cggaagcata agtgtaaag cctggggtgc ctaatgagtg     180
agctaactca cattaattgc gttgcgctca ctgcccgctt tccagtcggg aaaccctgtc     240
gtgccagctg cattaatgaa tcggccaacg cgcggggaga ggcggtttgc gtattgggcg     300
ccagggtggt ttttctttc accagtgaga cgggcaacag ctgattgccc ttcaccgcct     360
gggccctgag agagttgcag caagcggtcc acgctggttt gccccagcag gcgaaaatcc     420
tgtttgatgg tggttccgaa atcggcaaaa tcccttataa atcaaaagaa tagcccgaga     480
tagggttgag tgttgttcca gttttggaac aagagtccac tattaaagaa cgtggactcc     540
aacgtcaaag ggcgaaaaac cgtctatcag ggcgatgggc cactacgtga acatcaccaa     600
atcaagtttt tggggtcgag tgccgtaa                                       628

<210> SEQ ID NO 15
<211> LENGTH: 834
<212> TYPE: PRT
<213> ORGANISM: Thermus caldophilus

<400> SEQUENCE: 15
```

Met Glu Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
    65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Asn Pro Glu Lys Glu Gly Tyr Glu Val Arg Ile Leu Thr Ala Asp Arg
    130                 135                 140

-continued

```
Asp Leu Asp Gln Leu Val Ser Asp Arg Val Ala Val Leu His Pro Glu
145                 150                 155                 160
Gly His Leu Ile Thr Pro Glu Trp Leu Trp Gln Lys Tyr Gly Leu Lys
            165                 170                 175
Pro Glu Gln Trp Val Asp Phe Arg Ala Leu Val Gly Asp Pro Ser Asp
            180                 185                 190
Asn Leu Pro Gly Val Lys Gly Ile Gly Glu Lys Thr Ala Leu Lys Leu
            195                 200                 205
Leu Lys Glu Trp Gly Ser Leu Glu Asn Leu Leu Lys Asn Leu Asp Arg
    210                 215                 220
Val Lys Pro Glu Asn Val Arg Glu Lys Ile Lys Ala His Leu Glu Asp
225                 230                 235                 240
Leu Arg Leu Ser Leu Glu Leu Ser Arg Val Arg Thr Asp Leu Pro Leu
                245                 250                 255
Glu Val Asp Leu Ala Gln Gly Arg Glu Pro Asp Arg Glu Gly Leu Arg
                260                 265                 270
Ala Phe Leu Glu Arg Leu Glu Phe Gly Ser Leu Leu His Glu Phe Gly
    275                 280                 285
Leu Leu Glu Ala Pro Ala Pro Leu Glu Glu Ala Pro Trp Pro Pro Pro
    290                 295                 300
Glu Gly Ala Phe Val Gly Phe Val Leu Ser Arg Pro Glu Pro Met Trp
305                 310                 315                 320
Ala Glu Leu Lys Ala Leu Ala Ala Cys Arg Asp Gly Arg Val His Arg
                325                 330                 335
Ala Ala Asp Pro Leu Ala Gly Leu Lys Asp Leu Lys Glu Val Arg Gly
            340                 345                 350
Leu Leu Ala Lys Asp Leu Ala Val Leu Ala Ser Arg Glu Gly Leu Asp
            355                 360                 365
Leu Val Pro Gly Asp Asp Pro Met Leu Leu Ala Tyr Leu Leu Asp Pro
    370                 375                 380
Ser Asn Thr Thr Pro Glu Gly Val Ala Arg Arg Tyr Gly Gly Glu Trp
385                 390                 395                 400
Thr Glu Asp Ala Ala His Arg Ala Leu Leu Ser Glu Arg Leu His Arg
                405                 410                 415
Asn Leu Leu Lys Arg Leu Gln Gly Glu Glu Lys Leu Leu Trp Leu Tyr
                420                 425                 430
His Glu Val Glu Lys Pro Leu Ser Arg Val Leu Ala His Met Glu Ala
            435                 440                 445
Thr Gly Val Arg Leu Asp Val Ala Tyr Leu Gln Ala Leu Ser Leu Glu
    450                 455                 460
Leu Ala Glu Glu Ile Arg Arg Leu Glu Glu Glu Val Phe Arg Leu Ala
465                 470                 475                 480
Gly His Pro Phe Asn Leu Asn Ser Arg Asp Gln Leu Glu Arg Val Leu
                485                 490                 495
Phe Asp Glu Leu Arg Leu Pro Ala Leu Gly Lys Thr Gln Lys Thr Gly
            500                 505                 510
Lys Arg Ser Thr Ser Ala Ala Val Leu Glu Ala Leu Arg Glu Ala His
    515                 520                 525
Pro Ile Val Glu Lys Ile Leu Gln His Arg Glu Leu Thr Lys Leu Lys
            530                 535                 540
Asn Thr Tyr Val Asp Pro Leu Pro Ser Leu Val His Pro Asn Thr Gly
545                 550                 555                 560
```

-continued

```
Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
            610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Pro Pro Glu Ala Val
                645                 650                 655

Asp Pro Leu Met Arg Arg Ala Ala Lys Thr Val Asn Phe Gly Val Leu
                660                 665                 670

Tyr Gly Met Ser Ala His Arg Leu Ser Gln Glu Leu Ala Ile Pro Tyr
            675                 680                 685

Glu Glu Ala Val Ala Phe Ile Glu Arg Tyr Phe Gln Ser Phe Pro Lys
690                 695                 700

Val Arg Ala Trp Ile Glu Lys Thr Leu Glu Glu Gly Lys Arg Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
                740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
770                 775                 780

Val His Asp Glu Leu Leu Leu Glu Ala Pro Gln Ala Gly Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly
```

<210> SEQ ID NO 16
<211> LENGTH: 831
<212> TYPE: PRT
<213> ORGANISM: Thermus flavus

<400> SEQUENCE: 16

```
Met Ala Met Leu Pro Leu Phe Glu Pro Lys Gly Arg Val Leu Leu Val
 1               5                  10                  15

Asp Gly His His Leu Ala Tyr Arg Thr Phe Phe Ala Leu Lys Gly Leu
                20                  25                  30

Thr Thr Ser Arg Gly Glu Pro Val Gln Ala Val Tyr Gly Phe Ala Lys
            35                  40                  45

Ser Leu Leu Lys Ala Leu Lys Glu Asp Gly Asp Val Val Val Val Val
        50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95
```

```
Leu Ile Lys Glu Leu Val Asp Leu Leu Gly Leu Val Arg Leu Glu Val
        100                 105                 110
Pro Gly Phe Glu Ala Asp Val Leu Ala Thr Leu Ala Lys Arg Ala
        115                 120                 125
Glu Lys Glu Gly Tyr Glu Val Arg Ile Leu Thr Ala Asp Arg Asp Leu
        130                 135                 140
Tyr Gln Leu Leu Ser Glu Arg Ile Ala Ile Leu His Pro Gly Tyr
145                 150                 155                 160
Leu Ile Thr Pro Ala Trp Leu Tyr Glu Lys Tyr Gly Leu Arg Pro Glu
                165                 170                 175
Gln Trp Val Asp Tyr Arg Ala Leu Ala Gly Asp Pro Ser Asp Asn Ile
                180                 185                 190
Pro Gly Val Lys Gly Ile Gly Glu Lys Thr Ala Gln Arg Leu Ile Arg
                195                 200                 205
Glu Trp Gly Ser Leu Glu Asn Leu Phe Gln His Leu Asp Gln Val Lys
        210                 215                 220
Pro Ser Leu Arg Glu Lys Leu Gln Ala Gly Met Glu Ala Leu Ala Leu
225                 230                 235                 240
Ser Arg Lys Leu Ser Gln Val His Thr Asp Leu Pro Leu Glu Val Asp
                245                 250                 255
Phe Gly Arg Arg Arg Thr Pro Asn Leu Glu Gly Leu Arg Ala Phe Leu
                260                 265                 270
Glu Arg Leu Glu Phe Gly Ser Leu Leu His Glu Phe Gly Leu Leu Glu
        275                 280                 285
Gly Pro Lys Ala Ala Glu Glu Ala Pro Trp Pro Pro Glu Gly Ala
        290                 295                 300
Phe Leu Gly Phe Ser Phe Ser Arg Pro Glu Pro Met Trp Ala Glu Leu
305                 310                 315                 320
Leu Ala Leu Ala Gly Ala Trp Glu Gly Arg Leu His Arg Ala Gln Asp
                325                 330                 335
Pro Leu Arg Gly Leu Arg Asp Leu Lys Gly Val Arg Gly Ile Leu Ala
                340                 345                 350
Lys Asp Leu Ala Val Leu Ala Leu Arg Glu Gly Leu Asp Leu Phe Pro
        355                 360                 365
Glu Asp Asp Pro Met Leu Leu Ala Tyr Leu Leu Asp Pro Ser Asn Thr
        370                 375                 380
Thr Pro Glu Gly Val Ala Arg Arg Tyr Gly Gly Glu Trp Thr Glu Asp
385                 390                 395                 400
Ala Gly Glu Arg Ala Leu Leu Ala Glu Arg Leu Phe Gln Thr Leu Lys
                405                 410                 415
Glu Arg Leu Lys Gly Glu Glu Arg Leu Leu Trp Leu Tyr Glu Glu Val
        420                 425                 430
Glu Lys Pro Leu Ser Arg Val Leu Ala Arg Met Glu Ala Thr Gly Val
        435                 440                 445
Arg Leu Asp Val Ala Tyr Leu Gln Ala Leu Ser Leu Glu Val Glu Ala
        450                 455                 460
Glu Val Arg Gln Leu Glu Glu Val Phe Arg Leu Ala Gly His Pro
465                 470                 475                 480
Phe Asn Leu Asn Ser Arg Asp Gln Leu Glu Arg Val Leu Phe Asp Glu
                485                 490                 495
Leu Gly Leu Pro Ala Ile Gly Lys Thr Glu Lys Thr Gly Lys Arg Ser
                500                 505                 510
Thr Ser Ala Ala Val Leu Glu Ala Leu Arg Glu Ala His Pro Ile Val
```

-continued

```
            515                 520                 525
Asp Arg Ile Leu Gln Tyr Arg Glu Leu Thr Lys Leu Lys Asn Thr Tyr
        530                 535                 540

Ile Asp Pro Leu Pro Ala Leu Val His Pro Lys Thr Gly Arg Leu His
545                 550                 555                 560

Thr Arg Phe Asn Gln Thr Ala Thr Ala Thr Gly Arg Leu Ser Ser Ser
                565                 570                 575

Asp Pro Asn Leu Gln Asn Ile Pro Val Arg Thr Pro Leu Gly Gln Arg
            580                 585                 590

Ile Arg Arg Ala Phe Val Ala Glu Gly Trp Val Leu Val Val Leu
        595                 600                 605

Asp Tyr Ser Gln Ile Glu Leu Arg Val Leu Ala His Leu Ser Gly Asp
        610                 615                 620

Glu Asn Leu Ile Arg Val Phe Gln Glu Gly Arg Asp Ile His Thr Gln
625                 630                 635                 640

Thr Ala Ser Trp Met Phe Gly Val Ser Pro Glu Gly Val Asp Pro Leu
                645                 650                 655

Met Arg Arg Ala Ala Lys Thr Ile Asn Phe Gly Val Leu Tyr Gly Met
        660                 665                 670

Ser Ala His Arg Leu Ser Gly Glu Leu Ser Ile Pro Tyr Glu Glu Ala
        675                 680                 685

Val Ala Phe Ile Glu Arg Tyr Phe Gln Ser Tyr Pro Lys Val Arg Ala
        690                 695                 700

Trp Ile Glu Gly Thr Leu Glu Glu Gly Arg Arg Arg Gly Tyr Val Glu
705                 710                 715                 720

Thr Leu Phe Gly Arg Arg Arg Tyr Val Pro Asp Leu Asn Ala Arg Val
                725                 730                 735

Lys Ser Val Arg Glu Ala Ala Glu Arg Met Ala Phe Asn Met Pro Val
        740                 745                 750

Gln Gly Thr Ala Ala Asp Leu Met Lys Leu Ala Met Val Arg Leu Phe
        755                 760                 765

Pro Arg Leu Gln Glu Leu Gly Ala Arg Met Leu Leu Gln Val His Asp
770                 775                 780

Glu Leu Val Leu Glu Ala Pro Lys Asp Arg Ala Glu Arg Val Ala Ala
785                 790                 795                 800

Leu Ala Lys Glu Val Met Glu Gly Val Trp Pro Leu Gln Val Pro Leu
                805                 810                 815

Glu Val Glu Val Gly Leu Gly Asp Trp Leu Ser Ala Lys Glu
            820                 825                 830

<210> SEQ ID NO 17
<211> LENGTH: 834
<212> TYPE: PRT
<213> ORGANISM: Thermus oshimai

<400> SEQUENCE: 17

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60
```

```
Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
                100                 105                 110

Glu Val Pro Gly Phe Glu Ala Asp Asp Val Leu Ala Thr Leu Ala Lys
            115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
            245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro Pro
290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Lys Glu Gly Arg Val His Arg
                325                 330                 335

Ala Lys Asp Pro Leu Ala Gly Leu Lys Asp Leu Lys Glu Val Arg Gly
            340                 345                 350

Leu Leu Ala Lys Asp Leu Ala Val Leu Ala Leu Arg Glu Gly Leu Asp
            355                 360                 365

Leu Ala Pro Ser Asp Asp Pro Met Leu Leu Ala Tyr Leu Leu Asp Pro
370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ala Glu Arg Leu Gln Gln
                405                 410                 415

Asn Leu Leu Glu Arg Leu Lys Gly Glu Glu Lys Leu Leu Trp Leu Tyr
            420                 425                 430

Gln Glu Val Glu Lys Pro Leu Ser Arg Val Leu Ala His Met Glu Ala
            435                 440                 445

Thr Gly Val Arg Leu Asp Val Ala Tyr Leu Lys Ala Leu Ser Leu Glu
            450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
```

```
                    485                 490                 495
Phe Asp Glu Leu Arg Leu Pro Ala Leu Gly Lys Thr Gln Lys Thr Gly
                500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
        530                 535                 540

Asn Thr Tyr Val Asp Pro Leu Pro Gly Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Ile Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
610                 615                 620

Ser Gly Asp Glu Asn Leu Ile Arg Val Phe Gln Glu Gly Lys Asp Ile
625                 630                 635                 640

His Thr Gln Thr Ala Ser Trp Met Phe Gly Val Ser Pro Glu Ala Val
                645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro His Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Ile Gly Glu Asp Trp Leu Ser Ala
            820                 825                 830

Lys Gly

<210> SEQ ID NO 18
<211> LENGTH: 833
<212> TYPE: PRT
<213> ORGANISM: Thermus filiformis

<400> SEQUENCE: 18

Met Thr Pro Leu Phe Asp Leu Glu Glu Pro Pro Lys Arg Val Leu Leu
 1               5                  10                  15

Val Asp Gly His His Leu Ala Tyr Arg Thr Phe Tyr Ala Leu Ser Leu
```

-continued

```
                  20                  25                  30
Thr Thr Ser Arg Gly Glu Pro Val Gln Met Val Tyr Gly Phe Ala Arg
         35                  40                  45
Ser Leu Leu Lys Ala Leu Lys Glu Asp Gly Gln Ala Val Val Val Val
     50                  55                  60
Phe Asp Ala Lys Ala Pro Ser Phe Arg His Glu Ala Tyr Glu Ala Tyr
 65                  70                  75                  80
Lys Ala Gly Arg Ala Pro Thr Pro Glu Asp Phe Pro Arg Gln Leu Ala
                 85                  90                  95
Leu Val Lys Arg Leu Val Asp Leu Leu Gly Leu Val Arg Leu Glu Ala
            100                 105                 110
Pro Gly Tyr Glu Ala Asp Asp Val Leu Gly Thr Leu Ala Lys Lys Ala
            115                 120                 125
Glu Arg Glu Gly Met Glu Val Arg Ile Leu Thr Gly Asp Arg Asp Phe
            130                 135                 140
Phe Gln Leu Leu Ser Glu Lys Val Ser Val Leu Leu Pro Asp Gly Thr
145                 150                 155                 160
Leu Val Thr Pro Lys Asp Val Gln Glu Lys Tyr Gly Val Pro Pro Glu
                165                 170                 175
Arg Trp Val Asp Phe Arg Ala Leu Thr Gly Asp Arg Ser Asp Asn Ile
                180                 185                 190
Pro Gly Val Ala Gly Ile Gly Glu Lys Thr Ala Leu Arg Leu Leu Ala
            195                 200                 205
Glu Trp Gly Ser Val Glu Asn Leu Leu Lys Asn Leu Asp Arg Val Lys
            210                 215                 220
Pro Asp Ser Leu Arg Arg Lys Ile Glu Ala His Leu Glu Asp Leu His
225                 230                 235                 240
Leu Ser Leu Asp Leu Ala Arg Ile Arg Thr Asp Leu Pro Leu Glu Val
                245                 250                 255
Asp Phe Lys Ala Leu Arg Arg Thr Pro Asp Leu Glu Gly Leu Arg
            260                 265                 270
Ala Phe Leu Glu Glu Leu Glu Phe Gly Ser Leu Leu His Glu Phe Gly
            275                 280                 285
Leu Leu Gly Gly Glu Lys Pro Arg Glu Glu Ala Pro Trp Pro Pro
290                 295                 300
Glu Gly Ala Phe Val Gly Phe Leu Leu Ser Arg Lys Glu Pro Met Trp
305                 310                 315                 320
Ala Glu Leu Leu Ala Leu Ala Ala Ser Glu Gly Arg Val His Arg
            325                 330                 335
Ala Thr Ser Pro Val Glu Ala Leu Ala Asp Leu Lys Glu Ala Arg Gly
            340                 345                 350
Phe Leu Ala Lys Asp Leu Ala Val Leu Ala Leu Arg Glu Gly Val Ala
            355                 360                 365
Leu Asp Pro Thr Asp Pro Leu Leu Val Ala Tyr Leu Leu Asp Pro
            370                 375                 380
Ala Asn Thr His Pro Glu Gly Val Ala Arg Arg Tyr Gly Gly Glu Phe
385                 390                 395                 400
Thr Glu Asp Ala Ala Glu Arg Ala Leu Leu Ser Glu Arg Leu Phe Gln
                405                 410                 415
Asn Leu Phe Pro Arg Leu Ser Glu Lys Leu Leu Trp Leu Tyr Gln Glu
            420                 425                 430
Val Glu Arg Pro Leu Ser Arg Val Leu Ala His Met Glu Ala Arg Gly
            435                 440                 445
```

-continued

```
Val Arg Leu Asp Val Pro Leu Leu Glu Ala Leu Ser Phe Glu Leu Glu
    450             455             460

Lys Glu Met Glu Arg Leu Glu Gly Val Phe Arg Leu Ala Gly His
465             470             475             480

Pro Phe Asn Leu Asn Ser Arg Asp Gln Leu Glu Arg Val Leu Phe Asp
                485             490             495

Glu Leu Gly Leu Thr Pro Val Gly Arg Thr Glu Lys Thr Gly Lys Arg
            500             505             510

Ser Thr Ala Gln Gly Ala Leu Glu Ala Leu Arg Gly Ala His Pro Ile
        515             520             525

Val Glu Leu Ile Leu Gln Tyr Arg Glu Leu Ser Lys Leu Lys Ser Thr
    530             535             540

Tyr Leu Asp Pro Leu Pro Arg Leu Val His Pro Arg Thr Gly Arg Leu
545             550             555             560

His Thr Arg Phe Asn Gln Thr Ala Thr Ala Thr Gly Arg Leu Ser Ser
                565             570             575

Ser Asp Pro Asn Leu Gln Asn Ile Pro Val Arg Thr Pro Leu Gly Gln
            580             585             590

Arg Ile Arg Lys Ala Phe Val Ala Glu Glu Gly Trp Leu Leu Leu Ala
        595             600             605

Ala Asp Tyr Ser Gln Ile Glu Leu Arg Val Leu Ala His Leu Ser Gly
    610             615             620

Asp Glu Asn Leu Lys Arg Val Phe Arg Glu Gly Lys Asp Ile His Thr
625             630             635             640

Glu Thr Ala Ala Trp Met Phe Gly Leu Asp Pro Ala Leu Val Asp Pro
                645             650             655

Lys Met Arg Arg Ala Ala Lys Thr Val Asn Phe Gly Val Leu Tyr Gly
            660             665             670

Met Ser Ala His Arg Leu Ser Gln Glu Leu Gly Ile Asp Tyr Lys Glu
        675             680             685

Ala Glu Ala Phe Ile Glu Arg Tyr Phe Gln Ser Phe Pro Lys Val Arg
    690             695             700

Ala Trp Ile Glu Arg Thr Leu Glu Glu Gly Arg Thr Arg Gly Tyr Val
705             710             715             720

Glu Thr Leu Phe Gly Arg Arg Arg Tyr Val Pro Asp Leu Ala Ser Arg
                725             730             735

Val Arg Ser Val Arg Glu Ala Ala Glu Arg Met Ala Phe Asn Met Pro
            740             745             750

Val Gln Gly Thr Ala Ala Asp Leu Met Lys Ile Ala Met Val Lys Leu
        755             760             765

Phe Pro Arg Leu Lys Pro Leu Gly Ala His Leu Leu Leu Gln Val His
    770             775             780

Asp Glu Leu Val Leu Glu Val Pro Glu Asp Arg Ala Glu Glu Ala Lys
785             790             795             800

Ala Leu Val Lys Glu Val Met Glu Asn Ala Tyr Pro Leu Asp Val Pro
                805             810             815

Leu Glu Val Glu Val Gly Val Gly Arg Asp Trp Leu Glu Ala Lys Gln
            820             825             830

Asp
```